US012629359B2

(12) United States Patent
Bellucci et al.

(10) Patent No.: US 12,629,359 B2
(45) Date of Patent: May 19, 2026

(54) STRUCTURAL ANALOGUES OF METHYLPHENIDATE AS PARKINSON'S DISEASE-MODIFYING AGENTS

(71) Applicants: UNIVERSITA' DEGLI STUDI DI BRESCIA, Brescia (IT); UNIVERSITA' DEGLI STUDI DI MILANO, Milan (IT)

(72) Inventors: Arianna Bellucci, Pralboino (IT); Francesca Longhena, Nuvolento (IT); Ermanno Valoti, Dalmine (IT); Valentina Straniero, Merate (IT); Andrea Casiraghi, Milan (IT)

(73) Assignees: UNIVERSITA' DEGLI STUDI DI BRESCIA, Brescia (IT); UNIVERSITA' DEGLI STUDI DI MILANO, Milan (IT)

( * ) Notice: Subject to any disclaimer, the term of this patent is extended or adjusted under 35 U.S.C. 154(b) by 546 days.

(21) Appl. No.: 18/006,927

(22) PCT Filed: Aug. 4, 2021

(86) PCT No.: PCT/EP2021/071717
§ 371 (c)(1),
(2) Date: Jan. 26, 2023

(87) PCT Pub. No.: WO2022/029151
PCT Pub. Date: Feb. 10, 2022

(65) Prior Publication Data
US 2023/0263791 A1 Aug. 24, 2023

(30) Foreign Application Priority Data
Aug. 5, 2020 (IT) ........................ 102020000019303

(51) Int. Cl.
*C07D 211/32* (2006.01)
*A61K 31/4458* (2006.01)
*A61P 25/16* (2006.01)

(52) U.S. Cl.
CPC .......... *A61K 31/4458* (2013.01); *A61P 25/16* (2018.01)

(58) Field of Classification Search
CPC .... C07D 211/32; A61K 31/4458; A61P 25/16
See application file for complete search history.

(56) References Cited

U.S. PATENT DOCUMENTS

| | | | | |
|---|---|---|---|---|
| 10,226,442 B2* | 3/2019 | Tsai | A61K 31/4439 | |
| 11,278,509 B2* | 3/2022 | Tsai | A23L 33/16 | |
| 2006/0183773 A1* | 8/2006 | Bar-Or | A61P 25/14 | 514/317 |
| 2014/0142140 A1* | 5/2014 | Bird | A61K 31/4166 | 548/321.1 |
| 2022/0273600 A1* | 9/2022 | Tsai | A61K 31/496 | |
| 2023/0193388 A1* | 6/2023 | Whitaker | A61P 25/28 | 435/6.11 |

FOREIGN PATENT DOCUMENTS

| | | |
|---|---|---|
| WO | 2005042101 A1 | 5/2005 |
| WO | 2011011528 A1 | 1/2011 |

OTHER PUBLICATIONS

Axten et al. "A stereoselective synthesis of dl-threo-methylphenidate: preparation and biological evaluation of novel analogues." The Journal of Organic Chemistry 63.26 (1998): 9628-9629.

Davies et al. "Synthesis of methylphenidate analogues and their binding affinities at dopamine and serotonin transport sites." Bioorganic & Medicinal Chemistry Letters 14.7 (2004): 1799-1802.

Deutsch et al. "Synthesis and pharmacology of potential cocaine antagonists. 2. structure-activity relationship studies of aromatic ring-substituted methylphenidate analogs." Journal of Medicinal Chemistry 39.6 (1996): 1201-1209.

Deutsch et al. "Synthesis and pharmacology of site specific cocaine abuse treatment agents: a new synthetic methodology for methylphenidate analogs based on the Blaise reaction." European Journal of Medicinal Chemistry 36.4 (2001): 303-311.

Faustini et al. "Alpha-synuclein/synapsin III pathological interplay boosts the motor response to methylphenidate." Neurobiology of disease 138 (2020): 104789.

Froimowitz et al. "Further evidence for a dopamine reuptake pharmacophore. The effect of N-methylation on threo-methylphenidate and its analogs." Bioorganic & Medicinal Chemistry Letters 7.9 (1997): 1213-1218.

Hoffman et al. "2D QSAR modeling and preliminary database searching for dopamine transporter inhibitors using genetic algorithm variable selection of Molconn Z descriptors." Journal of Medicinal Chemistry 43.22 (2000): 4151-4159.

(Continued)

*Primary Examiner* — Brenda L Coleman
(74) *Attorney, Agent, or Firm* — Leason Ellis LLP

(57) ABSTRACT

The present invention describes compounds of formula (A) for use as Parkinson's disease modifying-agents, said formula (A). Surprisingly it has been found that the compounds of the invention can significantly reduce alpha-synuclein aggregation and stimulate the functional interaction between al-pha-synuclein and Synapsin III.

(A)

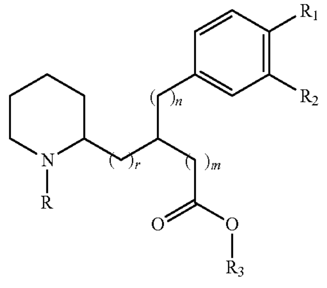

11 Claims, 9 Drawing Sheets

(56) References Cited

OTHER PUBLICATIONS

International Search Report and Written Opinion in corresponding International Patent Application No. PCT/EP2021/071717 mailed Nov. 3, 2021. 15 pages.
Misra et al. "Quantitative structure-activity relationship studies of threo-methylphenidate analogs." Bioorganic & Medicinal Chemistry 18.20 (2010): 7221-7238.
Moreau et al. "Methylphenidate for gait hypokinesia and freezing in patients with Parkinson's disease undergoing subthalamic stimulation: a multicentre, parallel, randomised, placebo-controlled trial." The Lancet Neurology 11.7 (2012): 589-596.
Thai et al. "Asymmetric synthesis and pharmacology of methylphenidate and its para-substituted derivatives." Journal of Medicinal Chemistry 41.4 (1998): 591-601.
Wayment et al. "Effects of methylphenidate analogues on phenethylamine substrates for the striatal dopamine transporter: potential as amphetamine antagonists?." Journal of Neurochemistry 72.3 (1999): 1266-1274.
Bellucci, "Synapsin III as a Novel Therapeutic Target in Parkinson's Disease", Website of Michael J Fox Foundation for Parkinson's Research, NY, USA (https://www.michaeljfox.org/grant/synapsin-iii-novel-therapeutic-target-parkinsons-disease-0) Aug. 15, 2020, (retrieved from Wayback Machine (https://web.archive.org/.com) on Oct. 22, 2025); 4 pages.
Ishikawa-Ankerhold et al. "Advanced fluorescence microscopy techniques—Frap, Flip, Flap, Fret and flim." Molecules 17.4 (2012): pp. 4047-4132.
Bellucci et al. "Alpha-synuclein aggregation and cell death triggered by energy deprivation and dopamine overload are counteracted by D2/D3 receptor activation." Journal of neurochemistry 106.2 (2008): pp. 560-577.
Gatley et al. "Place preference and microdialysis studies with two derivatives of methylphenidate." Life sciences 58.24 (1996): PL345-PL352; 8 pages.

* cited by examiner

FIG. 6

| | **I-threo** | **MPH** | Global (shared) |
|---|---|---|---|
| Comparison of Fits | | | |
| Null hypothesis | | | One curve for all data sets |
| Alternative hypothesis | | | Different curve for each data set |
| **P value** | | | **< 0.0001** |
| Conclusion (alpha = 0.05) | | | Reject null hypothesis |
| Preferred model | | | Different curve for each data set |
| F (DFn, DFd) | | | 56.18 (1,138) |
| | | | |
| Different curve for each data set | | | |
| Best-fit values | | | |
| LogEC50 | -6,365 | -4,428 | |
| **EC50** | **4,312e-007** | **3,733e-005** | |
| Std. Error | | | |
| LogEC50 | 0,06610 | 0,1273 | |
| 95% Confidence Intervals | | | |
| LogEC50 | -6.497 to -6.233 | -4.682 to -4.174 | |
| EC50 | 3.182e-007 to 5.843e-007 | 2.079e-005 to 6.701e-005 | |

FIG. 7

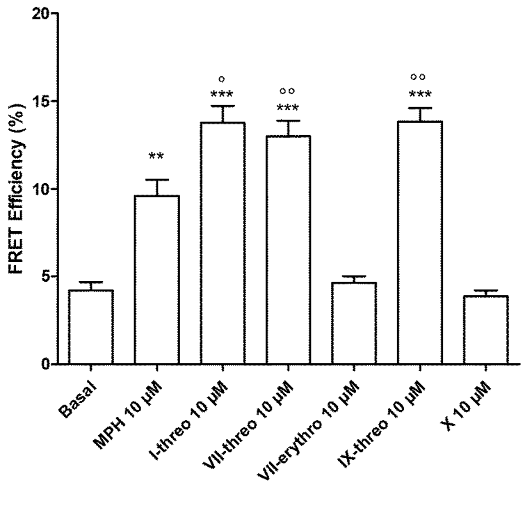

STRUCTURAL ANALOGUES OF METHYLPHENIDATE AS PARKINSON'S DISEASE-MODIFYING AGENTS

CROSS-REFERENCE TO RELATED PATENT APPLICATIONS

This application is a U.S. National Stage Application under 35 U.S.C. § 371 of International Patent Application No. PCT/EP2021/071717 filed Aug. 4, 2021, which claims the benefit of priority of Italian Patent Application No. 102020000019303 filed Aug. 5, 2020, both of which are incorporated by reference in their entireties. The International Application was published on Feb. 10, 2022, as International Publication No. WO 2022/029151 A1.

FIELD OF THE INVENTION

The present invention refers to the field of organic heterocyclic compounds, in particular analogues of methylphenidate (MPH), for use as Parkinson's disease modifying agents.

STATE OF THE ART

Parkinson's disease (PD) is the most common neurodegenerative movement disorder. The brain of affected patients is characterized by progressive loss of dopaminergic neurons of the substantia nigra and presence of Lewy bodies, proteinaceous inclusions mainly composed of fibrillary aggregates of the synaptic protein alpha-synuclein. It has been recently described that in the PD brains another synaptic protein named Synapsin III associates with alpha-synuclein to compose the insoluble fibrils forming Lewy Bodies. Aggregation and deposition of alpha-synuclein at synaptic sites are considered as the primum movens for the degeneration of dopaminergic neurons in Parkinson's disease and for the formation of Lewy bodies. Recent findings support that, besides composing Lewy bodies insoluble fibrils with alpha-synuclein, Synapsin III acts as a crucial mediator of alpha-synuclein aggregation and toxicity. Indeed, the lack of Synapsin III in a knock out mouse line impedes the development of alpha-synuclein insoluble aggregates and the related degeneration of dopaminergic nigrostriatal neurons prompted by the adeno-associated viral vectors-induced overexpression of human wild type alpha-synuclein. This supports that alpha-synuclein/Synapsin III interplay can constitute a new target for therapy in the context of Parkinson's disease.

Synapsin III and alpha-synuclein have been found to act as key regulators of nigrostriatal dopamine release and it was previously showed that they cooperatively exert this function. Methylphenidate (MPH), a monoamine reuptake inhibitor currently used for the treatment of attention deficits and hyperactivity disorder (ADHD), that can be associated with Synapsin III or alpha-synuclein polymorphisms, has been found to efficiently counteract freezing of gait in advanced Parkinson's disease. Notably, MPH displays alpha-synuclein binding ability and results able to stimulate alpha-synuclein-mediated dopamine neurotransmission, supporting that alpha-synuclein/Synapsin III interplay may influence the effect of this drug. On this line, Faustini, G et al. (Neurobiology of disease 2020, 138, 104789) found that threo-MPH was able to over-stimulate a Synapsin III-dependent locomotor activity, independently of its dopamine transporter inhibitory action, in an aged human alpha-synuclein transgenic mouse model of Parkinson's disease at a pathological stage exhibiting advanced alpha-synuclein/Synapsin III co-aggregates deposition and synaptic impairment. Remarkably, this effect was abolished by the gene silencing of Synapsin III. This evidence, when coupled to the fact that mice lacking alpha-synuclein do not exhibit locomotor stimulation upon MPH treatment, support that Synapsin III/alpha-synuclein pathological interplay boost the locomotor response to MPH.

To corroborate Synapsin III as a therapeutic target for PD was also performed its manipulation, by in vivo gene silencing, in a human alpha-synuclein transgenic mouse model of PD at an age exhibiting the typical phenotype (alpha-synuclein aggregates formation, striatal functional deficits and motor impairment). These studies were conducted with the support of the Michael J Fox Foundation for Parkinson's Research, NY, USA by Prof Arianna Bellucci. The findings of these studies support the validity of Synapsin III as a therapeutic target for PD as its manipulation by gene silencing at pathological stage can lead to disease modifying effects including reduction of alpha-synuclein aggregation, motor impairment recovery and dopamine neuron neuroprotection.

MPH analogues are known from Misra, M. et al. (*Bioorganic & medicinal chemistry* 2010, 18, 7221-7238), Froimowitz, M. et al. (*Bioorganic & Medicinal Chemistry Letters* 1997, 7, 1213-1218), Deutsch, H. M. et al. (*Journal of medicinal chemistry* 1996, 39, 1201-1209), Davies, H. M. L. (*Bioorganic & Medicinal Chemistry Letters* 2004, 14, 1799-1802), Thai, D. L. et al. (*Journal of medicinal chemistry* 1998, 41, 591-601), Deutsch, H. M. et al. (*European Journal of Medicinal Chemistry* 2001, 36, 303-311), Axten, J. M. et al. (*J. Org. Chem.* 1998, 63, 9628-9629); Wayment, H. K. et al. (*Journal of neurochemistry* 1999, 72, 1266-1274); Hoffman, B. T. et al. (*Journal of medicinal chemistry* 2000, 43, 4151-4159).

Aim of the present invention is to provide compounds for use as Parkinson's disease-modifying agents.

SUMMARY OF THE INVENTION

Subject of the present invention is a compound of formula (A) for use as Parkinson's disease modifying-agent, said formula (A)

(A)

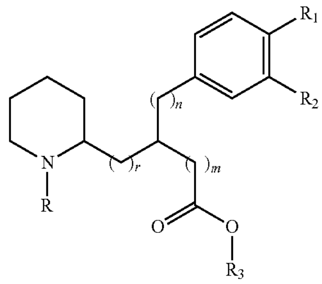

wherein

R is H, Alk;

$R_1$ is H, Alk, OAlk, Ar;

$R_2$ is H, Alk, OAlk, Ar;

$R_1$ and $R_2$ joined together can form an (hetero) aromatic ring;

$R_3$ is Me, Et, Pr and iPr;

n=0,1; m=0,1; r=0,1;

including pharmaceutical acceptable salt thereof, including threo and erythro racemates and (R,R) or (S,S) threo stereoisomers thereof, excluding methyl 2-phenyl-2-piperidin-2-ylacetate.

Surprisingly it has been found that the compounds of the invention can significantly reduce alpha-synuclein aggregation and stimulate the functional interaction between alpha-synuclein and Synapsin III and therefore own a significant disease modifying potential for the treatment of Parkinson's disease. The compounds of the inventions, by reducing alpha-synuclein aggregation and protecting nigrostriatal neurons, can exert a disease modifying effect in Parkinson's disease. In addition, they are able to stimulate the motor activity of Parkinson's disease mice, thus supporting that they can significantly improve Parkinson's disease motor symptoms. Therefore, a further subject-matter of the present invention is a pharmaceutical composition comprising a compound of formula (A) as above described and at least another pharmaceutically acceptable ingredient, said composition for use in the disease-modifying treatment of Parkinson's disease.

DETAILED DESCRIPTION OF THE INVENTION

According to the invention Alk means a linear or branched $C_1$-$C_4$ alkyl residue; preferably Me, Et.

According to the invention Ar means a 5 or 6 membered (hetero) aromatic ring, preferably Ph, thiophene or furane.

When $R_1$ and $R_2$ joined together to form an aromatic ring, said aromatic ring can be a 5 or 6 membered (hetero) aromatic ring, preferably Ph, thiophene or furane. According to the invention is preferred a compound of formula (A) as above defined wherein R is H, Me;

$R_1$ is H, Me, OMe, Ph;

$R_2$ is H, Me;

$R_1$ and $R_2$ joined together can form a phenyl ring.

A preferred compound of formula (A) is that wherein $R_1$ is other than H and $R_2$ is H; preferably $R_1$ is Alk.

A preferred compound of formula (A) is that having a threo configuration; and more preferably the (R,R) stereoisomer.

Preferably $R_3$ is Me.

Preferred salt according to the invention is HCl.

According to a particularly preferred embodiment of the invention a compound of formula (A) is, like compound I-threo, wherein R and $R_2$ are H; $R_1$ and $R_5$ are Me; is H; n=0; m=0; r=0.

According to another particularly preferred embodiment of the invention a compound of formula (A) is, like compound VI-threo, wherein R, $R_1$ and $R_3$ are Me, $R_2$ is H; n=0; m=0; r=0.

According to another particularly preferred embodiment of the invention a compound of formula (A) is, like compound VII-threo, wherein R, $R_1$ and $R_2$ are H; $R_3$ is Me n=1; m=0; r=0; or a pharmaceutical acceptable salt thereof.

Particularly preferred are compounds I-threo, VI-threo and VII-threo; more preferably the (R,R) isomers.

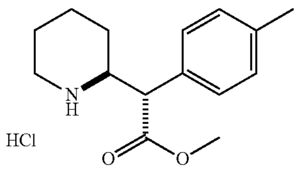

I-threo

-continued

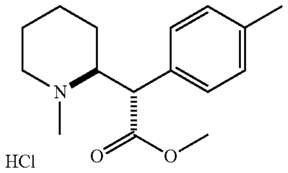

VI-threo

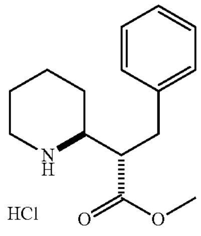

VII-threo

According to the present invention it has been observed that in particular the threo isomer modified on the phenyl moiety of MPH, such as I-threo, can significantly reduce alpha-synuclein aggregation and stimulate the functional interaction between alpha-synuclein and Synapsin III and therefore own a significant disease modifying potential for the treatment of Parkinson's disease.

The p-tolyl group, inserted in lieu of the phenyl ring, is structurally a quite mild modification; nevertheless, the biological evaluation surprisingly highlighted a relevant difference in the ability of I-threo to modulate alpha-synuclein/Synapsin III interaction.

Several factors could contribute to this worthwhile result, first of all the steric hindrance and the non-planarity of the methyl group in para position of the phenyl ring, which could reflect in a better interaction with the target protein. Moreover, also the formation of an additional bond between the methyl group and the binding pocket of Synapsin III could be responsible for the increase of the activity. Finally, the insertion of the methyl enhances also the lipophilicity of the whole molecule, and this increase could result in a modification not only of the permeability profile of I-threo, but also of other important parameters, that could modulate the interaction with Synapsin III and thus have a disease modifying effect in PD. In particular, by stimulating the functional interaction between Synapsin III and a specific alpha-synuclein conformation that is generated in the high lipid crowding environment that occurs within LB, I-threo and similar analogues deriving from the modification of MPH phenyl moiety, can reduce alpha-synuclein aggregation thus hampering the related synaptic deficits.

The present invention could be better understood by the following examples.

BRIEF DESCRIPTION OF THE FIGURES

FIG. 6 shows the table that summarizes the therapeutic efficacy and EC50 of compound I-threo in reducing alpha-synuclein aggregation in SK—N—SH cells compared with MPH.

FIG. 7 shows the graph that summarizes the effect of compounds VII-threo, VII-erytrho, IX-threo, X on alpha-synuclein/Synapsin III interaction by acceptor photobleaching FRET. ( P<0.01 vs.Basal; * P<0.001 vs.Basal; ° P<0.05 vs. MPH 10 μM; °° P<0.01 vs. MPH 10 M; One-way ANOVA+Newman-Keuls' post comparison test).

Experimental Section

MATERIALS AND METHODS

Figure 1:
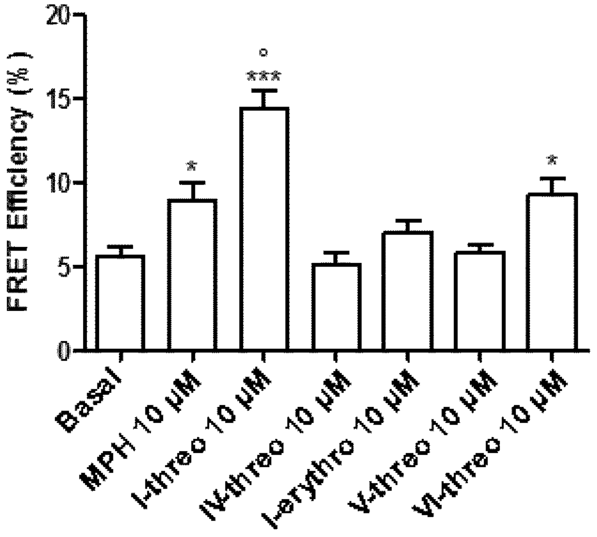
FIG. 1 shows histogram which summarizes the FRET efficiency upon the treatment with MPH and the compounds object of the present patent. I-threo induced a significant increase in the FRET efficiency both compared to basal level and MPH or VI-threo. No significant increase was observed for the IV-threo, I-erythro and V-threo compared to baseline. (* $P<0.05$ vs.Basal; *** $P<0.001$ vs.Basal; ° $P<0.05$ vs. MPH 10 UM; One-way ANOVA+Newman-Keuls' post comparison test).

- Melting points were measured either on a Büchi Melting Point B-540 apparatus or a TA Instruments Q20 DSC system;
- TLC were performed on standard analytical silica gel layers (thickness 0.20 mm; Macherey-Nagel ALUGRAM SIL G/UV254);
- Chromatographic purifications were performed, in normal phase, using Biotage instruments (Isolera or SP1) over different Biotage SNAP Ultra flash chromatography cartridges, filled of Merck Silica Gel 60 (0.040-0.063 μm). The final Compounds purity was assessed on HPLC by using Elite LaChrom HPLC system with diode array detector (190-400 nm) and a Waters XBridge™ C-18 column (5 μm, 4.6×150 mm). The specific method is here reported and proved to be effective in separating threo and erythro isomers.

| Time | Solvents % | | Flow rate |
|---|---|---|---|
| (minutes) | Water + TFA 1‰ | ACN + TFA ‰ | (mL/min) |
| 0 | 90% | 10% | 1 |
| 20 | 10% | 90% | 1 |
| 25 | 10% | 90% | 1 |
| 30 | 90% | 10% | 1 |
| 35 | 90% | 10% | 1 |

The HPLC method was set up using a Waters XBridge™ C-18 column flushed with freshly prepared 90% Water/10% ACN+TFA 1% % until column pressure was stable. All the investigated samples were prepared through dissolution of the purified products in the selected mobile phase, at the approximate concentrations of 1 mg/mL, filtered through a 0.45 μm filter and analysed. The injection volume was 20 μL. Owing to the presence of the substituted phenyl ring in each compound, purity was evaluated on chromatograms recorded at 217 nm and expressed as Area %. Abbreviations used: ACN: acetonitrile; DCM: dichloromethane; DMF: dimethylformamide; DMSO: dimethylsulfoxide; EDAC: 1-Ethyl-3-(3-dimethylaminopropyl) carbodiimide; EDTA: ethylenediaminetetraacetic acid; HOBt: hydroxy benzotriazole; IPA: isopropyl alcohol; IPE: diisopropylether; mp: melting point; MW: molecular weight; NBS: N-bromosuccinimide; RT: room temperature; TBTU: O-(benzotriazol-1-yl)-N,N,N',N'-tetramethyluronium tetrafluoroborate; TEA: triethylamine; TFA: trifluoroacetic acid; THF: tetrahydrofuran.

Chemical Synthesis of MPH Derivatives

The following compounds derivatives of MPH were synthesized:

TABLE 1

| Cpd# | Structure | Bibliography |
|---|---|---|
| I-threo | 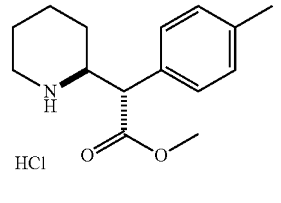 | Davies et al. 2004; Deutsch et al. 1996; Thai et al. 1998 |

TABLE 1-continued
| Cpd# | Structure | Bibliography |
| --- | --- | --- |
| I-erythro | 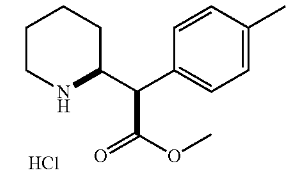 | Davies et al. 2004; Deutsch et al. 1996; Thai et al. 1998 |
| II-threo | 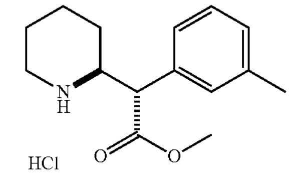 | Misra et al. 2010; Deutsch et al. 1996 |
| II-erythro | 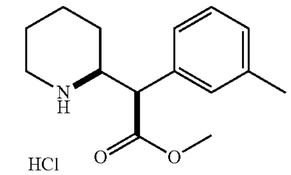 | Deutsch et al. 1996 |
| III-threo | 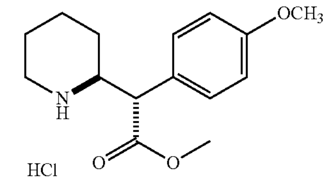 | Misra et al. 2010; Deutsch et al. 1996; Gatley et al. 1996 |
| IV-threo | 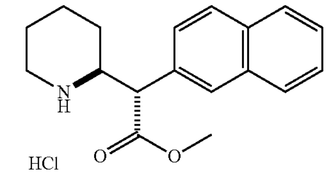 | Misra et al. 2010; Davies et al. 2004; Deutsch et al. 2001; Axten et al. 1998 |
| IV-erythro | 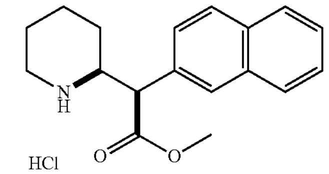 | Davies et al. 2004; Deutsch et al. 2001; |
| V-threo | 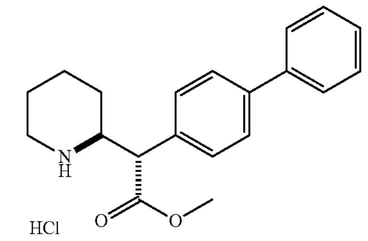 | Davies et al. 2004 |
| V-erythro | 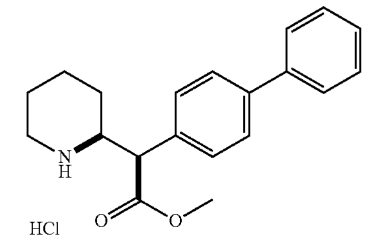 | Davies et al. 2004 |

TABLE 1-continued
| Cpd# | Structure | Bibliography |
|---|---|---|
| VI-threo | 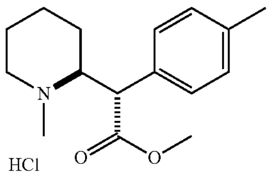 | Misra et al. 2010; Froimowitz et al. 1997; Wayment et al. 1999 |
| VII-threo | 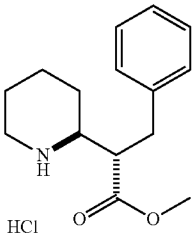 | Deutsch et al. 2001; Axten et al. 1998 |
| VII-erythro | 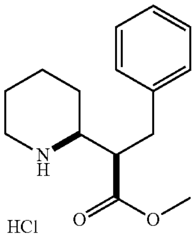 | |
| VIII-threo | 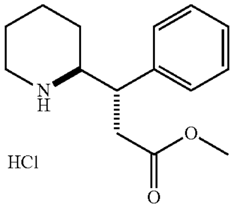 | Hoffman et al. 2000 |
| VIII-erythro | 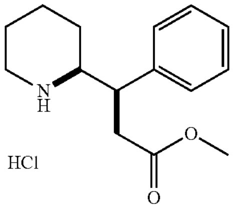 | |
| IX-threo | 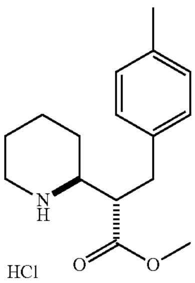 | |

TABLE 1-continued

| Cpd# | Structure | Bibliography |
|---|---|---|
| IX-erythro | 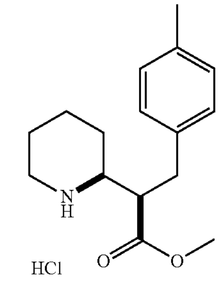 | |
| X | 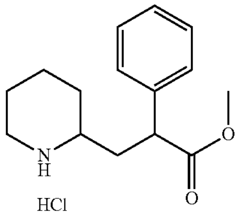 [SMILES: COC(=O)C(CC1CCCCN1)c1ccccc1 ; Cl] | |

Here after are reported all the general procedures for obtaining the presented derivatives, together with an example for each scheme. In the reaction in which the two isomers (threo and erythro) were obtained and isolated, the experimental data for both were reported. The following synthetic steps were the same for both the isomers but the experimental data were reported for a single compound.

SCHEME 1: general procedure for the synthesis of compounds I, IV, V and VI.

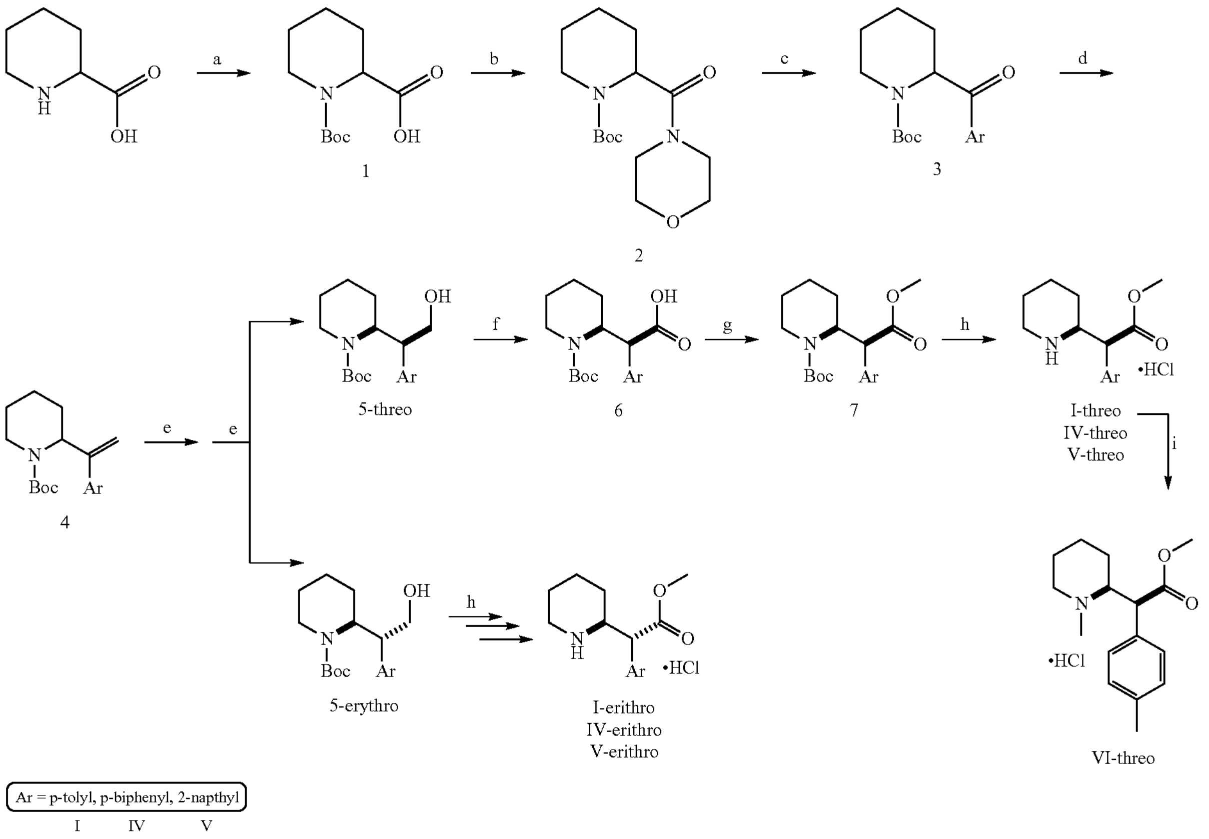

Reagents and conditions: (a) $Boc_2O$, TEA, MeOH, 50° C./RT; (b) TBTU, TEA, morpholine, RT; (c) ArBr, n-BuLi, THF, -78° C.; (d) $PPh_3CH_3Br$, t-BuOK, THF, RT; (e) $BH_3$•THF, $H_20$, NaOH, $H_2O_2$, THF, RT, (f) PDC, DMF, RT; (g) $TMSCHN_2$, toluene, MeOH; (h) HCl/MeOH, RT to 60° C.; (i) AcOH, formaldehyde, Pd/C, $H_2$ (2.5 atm), MeOH, RT.

The synthesis started from commercially available racemic pipecolic acid, whose amine function was protected with Boc carbonate (1), prior to conversion into the corresponding morpholine amide 2, using TBTU as coupling agent. The consecutive reaction with the suitably substituted aryl lithium salt, generated in situ by the treatment of the corresponding aryl bromides with n-BuLi, afforded aryl ketones 3. The carbonyl function then underwent Wittig reaction with methyltriphenylphosphonium bromide, accomplishing vinyl aryl derivatives 4, which were then converted into the respective primary alcohols 5 via hydroboration. At this stage, the threo and erythro racemates, resulting from the generation of the second stereocenter, were readily isolated through separation on column chromatography in silica gel, and then oxidized to the corresponding carboxylic acids 6. Subsequent reaction with trimethylsilyldiazomethane led to accomplish methyl esters 7, whose amine function underwent deprotection in acidic conditions, affording compounds I, IV and V. The treatment of I-threo with formaldehyde in methanol and the consecutive reduction with hydrogen in presence of Pd/C and acetic acid yielded compound VI-threo.

Synthesis of Compound (I-Threo), Following SCHEME 1 N-Boc Pipecolic Acid (1)

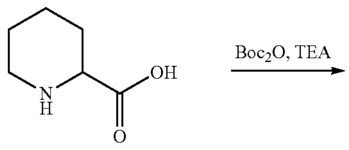

$C_6H_{11}NO_2$
MW: 129,16

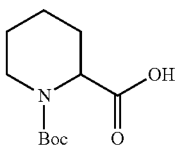

$C_{11}H_{19}NO_4$
MW: 229,27

Pipecolic acid (10.0 g, 77.4 mmol) was dissolved in MeOH (50 mL) and TEA (11.9 mL, 85.2 mmol) was added. The mixture was heated up to 50° C. and a solution of $Boc_2O$ (33.8 g, 155 mmol) in MeOH (50 mL) was added. After stirring at RT for 20 hours, MeOH was evaporated under reduced pressure, the residue was taken up in ethyl acetate (90 mL) and extracted with 10% $NaHCO_3$ (3x30 mL). The aqueous phase was acidified to pH=1 with 37% HCl and the white precipitate was filtered and washed with water to afford 16.2 g (92%) of N-Boc pipecolic acid as a white solid (mp: 130-133° C.).

$^1$H NMR (300 MHz, $CDCl_3$): δ4.83 (bs, 1H), 4.14-3.81 (m, 1H), 3.06-2.79 (m, 1H), 2.29-2.10 (m, 1H), 1.75-1.11 (m, 15H).

N-Boc Pipecolic Acid Morpholine Amide (2)

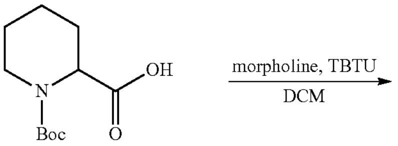

1
$C_{11}H_{19}NO_4$
MW: 229,27

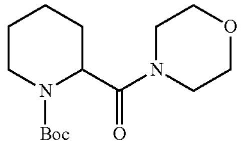

2
$C_{15}H_{26}N_2O_4$
MW: 298,38

N-Boc pipecolic acid (1) (7.80 g, 34.0 mmol), TBTU (14.20 g, 44.2 mmol) and TEA (6.64 mL, 47.6 mmol) were suspended in DCM (80 mL) and stirred at RT for 30 minutes. Morpholine (4.16 mL, 47.63 mmol) was added and the mixture was stirred at RT for 24 hours. The organic phase was washed with 10% HCl (25 mL), 10% $NaHCO_3$ (25 mL) and saturated NaCl (25 mL) and the organic phase was dried over $MgSO_4$ and evaporated under reduced pressure. Rotary evaporation was protracted to remove leftover tetramethyl urea and gave 8.58 g (85%) of N-Boc pipecolic acid morpholine amide (2) as a light orange waxy solid.

$^1$H NMR (300 MHz, $CDCl_3$): δ5.00-4.56 (m, 1H), 3.84 (d, J=12.3 Hz, 1H), 3.71-3.29 (m, 8H), 3.18 (t, J=12.4 Hz, 1H), 1.90-1.49 (m, 5H), 1.38 (s, 10H).

N-Boc-piperidin-2-yl(p-tolyl)methanone (3)

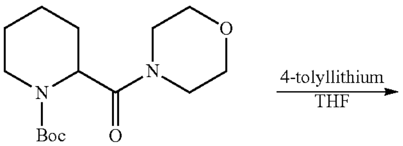

2
$C_{15}H_{26}N_2O_4$
MW: 298,38

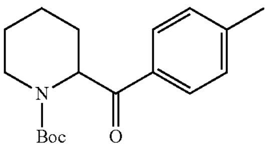

3
$C_{18}H_{25}NO_3$
MW: 303,40

2.7M n-BuLi (10.4 mL, 28.2 mmol) was added dropwise to a solution of 4-bromotoluene (4.82 g, 28.2 mmol) in anhydrous THF (50 mL) at −78° C. under nitrogen atmosphere. The mixture was stirred at the same temperature for 30 minutes and a solution of N-Boc pipecolic acid morpholine amide (2) (2.80 g, 9.39 mmol) in anhydrous THF (30 mL) was added. After stirring for 4.5 hours, the reaction was quenched at −78° C. with a solution of 10% HCl (9 mL) in MeOH (20 mL). The mixture was brought to RT and ethyl acetate (50 mL) and phosphate buffer (50 mL) were added.

THF was evaporated under reduced pressure, phases were separated, and the aqueous phase was extracted with ethyl acetate (2×25 mL). The collected organic phases were dried over $MgSO_4$ and evaporated under reduced pressure.

The obtained crude was purified by column chromatography on silica gel. Elution with cyclohexane/ethyl acetate 95:5 gave 1.99 g (70%) of N-Boc-piperidin-2-yl(p-tolyl) methanone (3) as a white solid (mp: 95-97° C.).

$^1H$ NMR (300 MHz, $CDCl_3$): δ7.81 (d, J=7.7 Hz, 2H), 7.23 (d, J=7.7 Hz, 2H), 5.70-5.41 (m, 1H), 4.05-3.84 (m, 1H), 3.28-3.06 (m, 1H), 2.40 (s, 3H), 2.20-1.95 (m, 1H), 1.91-1.71 (m, 1H), 1.72-1.23 (m, 13H).

N-Boc-2-(1-(p-tolyl)vinyl)piperidine (4)

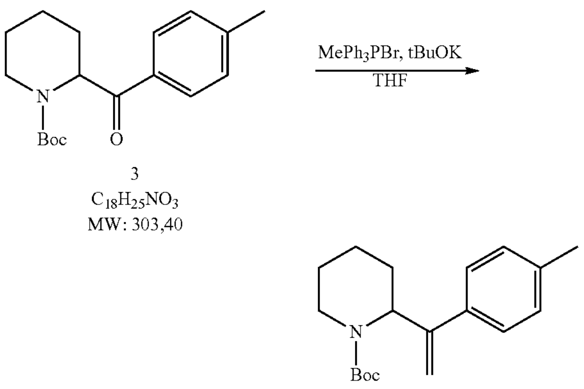

3
$C_{18}H_{25}NO_3$
MW: 303,40

4
$C_{19}H_{27}NO_2$
MW: 301,42

Potassium tert-butylate (0.69 g, 6.18 mmol) was added to a solution of methyltriphenylphosphonium bromide (2.21 g, 6.18 mmol) in anhydrous THF (10 mL) under nitrogen atmosphere. After stirring for 10 minutes, a solution of 3 (1.25 g, 4.12 mmol) in THF (5 ml) was added dropwise. After stirring at RT for 4 hours, the reaction was quenched with water (50 mL) and extracted with ethyl acetate (3×20 mL). The organic phase was dried over $MgSO_4$, evaporated under reduced pressure and the obtained crude was purified by filtration on silica gel plug (eluent cyclohexane/ethyl acetate 7:3) to give 0.97 g (90%) of N-Boc-2-(1-(p-tolyl) vinyl)piperidine (4) as colourless oil.

$^1H$ NMR (300 MHz, $CDCl_3$): δ7.14 (d, J=8.0 Hz, 2H), 7.04 (d, J=8.2 Hz, 2H), 5.16 (s, 1H), 5.25-5.11 (m, 1H), 4.92 (s, 1H), 3.97-3.81 (m, 1H), 2.89-2.75 (m, 1H), 2.26 (s, 3H), 1.80-1.67 (m, 1H), 1.62-1.44 (m, 2H), 1.45-1.26 (m, 12H).

N-Boc-2-(piperidin-2-yl)-2-(p-tolyl)ethanol (5-threo and 5-erythro)

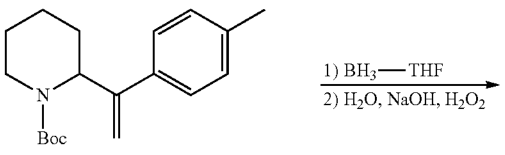

4
$C_{19}H_{27}NO_2$
MW: 301,42

-continued

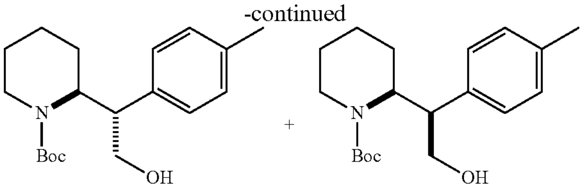

5-threo 5-erythro $C_{19}H_{29}NO_3$
MW: 319,44

1M borane THF complex (22.9 mL, 22.9 mmol) was added dropwise to a solution of N-Boc-2-(1-(p-tolyl)vinyl) piperidine (4) (3.45 g, 11.4 mmol) in anhydrous THF (50 mL) under nitrogen atmosphere. The mixture was stirred at RT overnight and water (20 mL), 2.5N NaOH (20 mL) and 35% $H_2O_2$ (40 mL) were added in succession and stirring was continued for additional 4 hours. Water (40 mL) was added and the mixture was extracted with ethyl acetate (3×50 mL). The organic phase was washed with 5% sodium bisulfite (50 mL), dried over $MgSO_4$ and evaporated under reduced pressure. The obtained crude was purified by column chromatography on silica gel. Elution with cyclohexane/ethyl acetate 90:10 gave 1.54 g (42%) of threo N-Boc-2-(piperidin-2-yl)-2-(p-tolyl)ethanol (5-threo) as a white solid (mp: 138-141° C.) and 0.12 g (22%) of erythro N-Boc-2-(piperidin-2-yl)-2-(p-tolyl)ethanol (5-erythro) as a colorless oil.

(5-threo) $^1H$ NMR (300 MHz, $CDCl_3$): δ7.23 (d, J=6.4 Hz, 2H), 7.13 (d, J=7.9 Hz, 2H), 4.63-4.21 (m, 1H), 4.10-3.83 (m, 1H), 3.75-3.61 (m, 1H), 3.62-3.39 (m, 1H), 3.11-2.89 (m, 1H), 2.77 (dt, J=13.2, 2.9 Hz, 1H), 2.26 (s, 3H), 1.65-1.17 (m, 15H).

(5-erythro) $^1H$ NMR (300 MHz, $CDCl_3$): δ7.13 (d, J=8.2 Hz, 2H), 7.09 (d, J=8.2 Hz, 2H), 4.53-4.42 (m, 1H), 3.83 (dd, J=12.1, 5.9 Hz, 1H), 3.78-3.67 (m, 2H), 3.28-3.16 (m, 1H), 2.67-2.52 (m, 1H), 2.28 (s, 3H), 1.80-1.40 (m, 6H), 1.29 (s, 9H).

threo N-Boc-2-(piperidin-2-yl)-2-(p-tolyl)acetic acid (6-threo)

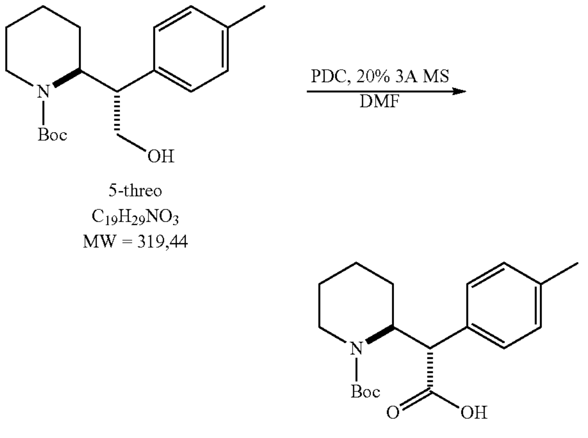

5-threo
$C_{19}H_{29}NO_3$
MW = 319,44

6-threo
$C_{19}H_{27}NO_4$
MW =: 333,42

Pyridinium dichromate (0.62 g, 1.64 mmol) and 3 Å molecular sieves (0.03 g) were added to a solution of threo N-Boc-2-(piperidin-2-yl)-2-(p-tolyl)ethanol (5-threo) (0.15 g, 0.47 mmol) in DMF (2 mL) and the mixture was stirred at RT overnight. Ethyl ether (5 mL) was added and the reaction was quenched by adding 10% HCl (5 mL) dropwise at 0° C. The aqueous phase was extracted with ethyl ether (3x5 mL) and the collected organic phases were extracted with 10% NaOH (3x10 mL). The collected aqueous phases were brought to pH=1 with conc. HCl and extracted with DCM (3x15 mL). The collected organic phases were dried over $MgSO_4$ and evaporated under reduced pressure to give 0.11 g (70%) of threo N-Boc-2-(piperidin-2-yl)-2-(p-tolyl) acetic acid (6-threo) as a white waxy solid. $^1H$ NMR (300 MHz, $CDCl_3$): δ7.37 (d, J=11.0 Hz, 2H), 7.07 (d, J=11.0 Hz, 2H), 4.85-4.80 (m, 1H), 4.02 (d, J=16.2 Hz, 1H), 4.05-3.90 (m, 1H), 3.29-3.13 (m, 1H), 2.28 (s, 3H), 1.75-1.17 (m, 6H), 1.48 (s, 9H).

threo N-Boc-methyl 2-(piperidin-2-yl)-2-(p-tolyl) acetate (7-threo)

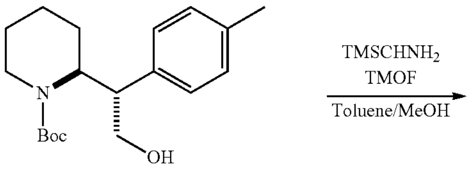

6-threo
$C_{19}H_{27}NO_4$
MW = 333,42

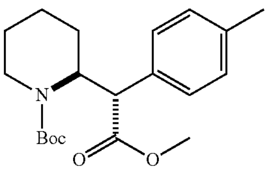

7-threo
$C_{20}H_{29}NO_4$
MW = 347,45

2M trimethylsilyldiazomethane (1.27 mL, 2.53 mmol) was added to a solution of threo N-Boc-2-(piperidin-2-yl)-2-(p-tolyl)acetic acid (6-threo) (0.65 g, 1.95 mmol) and trimethylorthoformate (2 mL) in toluene/MeOH (15 mL+15 mL) under nitrogen atmosphere. The mixture was stirred at RT overnight and solvents were evaporated under reduced pressure to give 0.60 g (88%) of threo N-Boc-methyl 2-(piperidin-2-yl)-2-(p-tolyl)acetate (7-threo) as a green/brown oil. $^1H$ NMR (300 MHz, $CDCl_3$): δ7.40-7.28 (m, 2H), 7.14 (d, J=7.9 Hz, 2H), 5.06-4.74 (m, 1H), 4.11 (d, J=11.7 Hz, 1H), 4.25-3.90 (m, 1H), 3.61 (s, 3H), 3.13-2.88 (m, 1H), 2.33 (s, 3H), 1.76-1.18 (m, 15H).

threo methyl 2-(piperidin-2-yl)-2-(p-tolyl)acetate hydrochloride (I-threo)

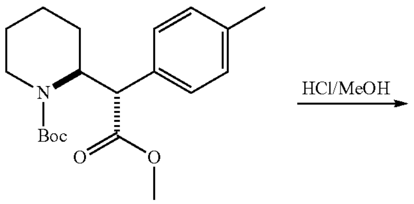

7-threo
$C_{20}H_{29}NO_4$
MW: 347,45

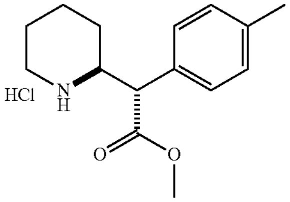

I-threo
$C_{15}H_{21}ClNO_2$
MW: 283.79 threo N-Boc-methyl 2-(piperidin-2-yl)-2-(p-tolyl)acetate (0.60 g, 1.72 mmol) was dissolved in excess 2N HCl/MeOH and stirred at RT for 1 hour. Solvents were evaporated under reduced pressure and the resulting crude was crystallized from toluene/MeOH 85:15 to give 0.22 g (44%) of threo methyl 2-(piperidin-2-yl)-2-(p-tolyl)acetate hydrochloride as a white solid (mp: 205° C. with decomposition). Retention Time (HPLC)=8.85'; HPLC Purity=96%.

$^1H$ NMR (300 MHz, $CD_3OD$): δ7.22 (d, J=8.0 Hz, 1H), 7.15 (d, J=8.1 Hz, 1H), 3.81-3.75 (m, 1H), 3.71 (s, 1H), 3.47-3.38 (m, 1H), 3.09 (dt, J=12.8, 9.5 Hz, 1H), 2.33 (s, 2H), 1.94-1.24 (m, 3H).

$^{13}C$ NMR (75 MHz, $CD_3OD$): δ 171.98, 138.46, 130.59, 129.60, 127.94, 57.85, 53.59, 51.94, 45.21, 26.34, 22.00, 21.34, 19.66.

threo methyl 2-(1-methylpiperidin-2-yl)-2-(p-tolyl) acetate hydrochloride (VI-threo)

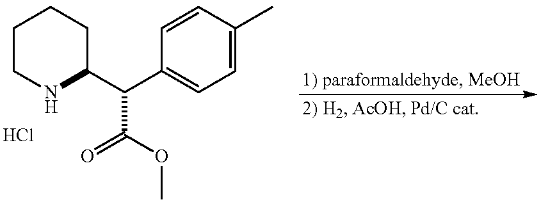

I-threo
$C_{14}H_{18}ClNO_2$
MW: 268,75

-continued

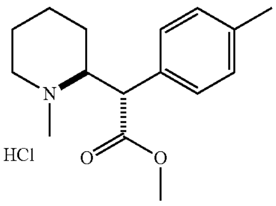

VI-threo
$C_{16}H_{23}NO_2$
MW: 297.81 threo methyl 2-(piperidin-2-yl)-2-(p-tolyl)acetate (I-threo) (260 mg, 0.91 mmol) was dissolved in MeOH (20 mL), 37% paraformaldehyde (0.09 mL, 1.18 mmol) was added and the mixture was stirred at RT for 20 minutes. Acetic acid (0.03 mL) and Pd/C (KF=50%) (90 mg) were added and the mixture was vigorously shaken under 2.5 atm hydrogen at RT for 2.5 hours. After filtering on a celite pad, solvents were evaporated under reduced pressure and the residue was taken up in ethyl acetate (20 mL) and washed with 10% $NaHCO_3$ (10 mL). The aqueous phase was extracted with ethyl acetate (2×5 mL) and the solvent was evaporated under reduced pressure. The oily residue was analysed by NMR, which confirmed its purity. $^1H$ NMR (freebase) (300 MHz, $CD_3OD$): δ7.17 (d, J=8.3 Hz, 2H), 7.12 (d, J=8.3 Hz, 2H), 3.74 (d, J=9.9 Hz, 1H), 3.63 (s, 3H), 3.21-3.07 (m, 1H), 2.93 (dt, J=9.1, 4.2 Hz, 1H), 2.59-2.43 (m, 1H), 2.38 (s, 3H), 2.30 (s, 3H), 1.66-1.46 (m, 3H), 1.37-1.13 (m, 2H), 1.12-0.86 (m, 1H).

$^{13}C$ NMR (freebase) (75 MHz, $CDCl_3$): δ174.50, 137.03, 129.26, 128.68, 63.35, 54.08, 54.02, 52.04, 40.83, 24.70, 22.97, 22.31, 21.03.

The free base was then treated with excess HCl/MeOH and the solvents were evaporated under reduced pressure. The resulting crude was treated with acetone (1 mL) to precipitate 47 mg (17%) threo methyl 2-(1-methylpiperidin-2-yl)-2-(p-tolyl)acetate hydrochloride (VI-threo) as a white solid (mp: 187° C. with decomposition). Retention Time (HPLC)=8.97'; HPLC Purity=98%.

SCHEME 2: general procedure for the synthesis of compounds II

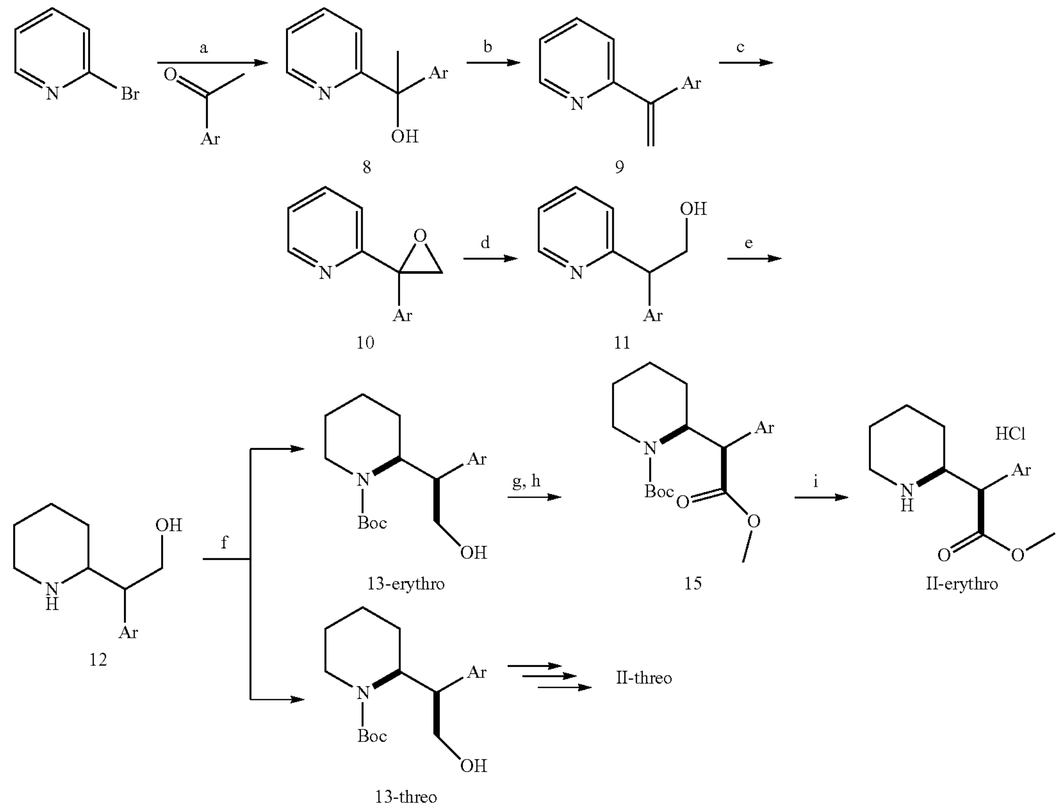

Ar = m-tolyl

Reagents and conditions: (a) n-BuLi, THF, -78° C. to -20° C.; (b) $H_2SO_4$; (c) 1- NBS, dioxane, $H_2O$, 2-NaOH, IPA; (d) $NH_4COOH$, Pd/C; (e) $H_2$ (5 atm), Pd/C, 70° C., AcOH, HCl/$Et_2O$; (f) $Boc_2O$, TEA, DCM; (g) TEMPO, $NaClO_2$, NaClO, DCM/phosphate buffer; (h) $TMSCHN_2$, toluene, MeOH; (i) HCl/MeOH.

In this alternative procedure, the formation of the C—C bond is obtained in the first step with the reaction of a suitable acetophenone with the 2-pyridil lithium salt, obtained in situ from 2-bromopyridine, to give the biaryl tertiary alcohols 8 with consistently good yields. In the following steps, 8 get easily dehydrated to afford the corresponding diaryl alkenes 9 and then converted into epoxides 10 in a 2-step hydroxybromination/substitution reaction. Regioselective reduction in Hydrogen Transfer conditions gives the primary alcohols 11, which in turn undergo Ptcatalysed hydrogenation of the pyridyl ring to yield piperidyl derivatives 12. Oxidation to carboxylic acids 14 in a TEMPO-mediated oxidation protocol and subsequent esterification and deprotection afford the final products (threo and erythro)

Synthesis of Compound II-Erythro, Following SCHEME 2 1-(pyridin-2-yl)-1-(m-tolyl)ethanol

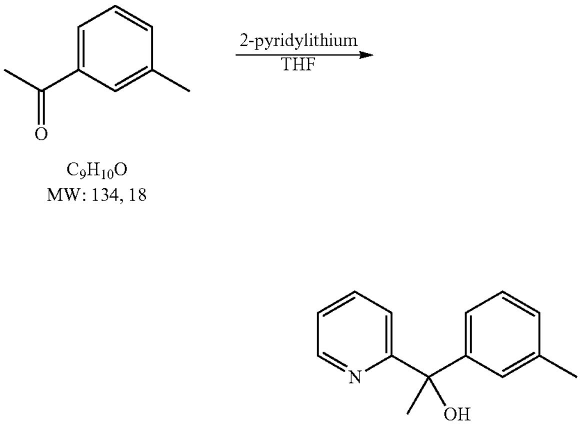

$C_9H_{10}O$
MW: 134, 18

8
$C_{14}H_{15}NO$
MW: 213,28

2.7M n-BuLi (8.67 mL, 23.4 mmol) was added dropwise to a solution of 2-bromopyridine (2.03 mL, 21.3 mmol) in anhydrous THF (15 mL) at −78° C. under nitrogen atmosphere. The mixture was stirred at the same temperature for 45 minutes and a solution of 3-methylacetophenone (3.10 g, 22.4 mmol) in anhydrous THF (15 mL) was added. Stirring was continued at −78° C. for 15 minutes and then the mixture was left stirring overnight at RT. The reaction was quenched with the addition of saturated $NH_4Cl$ (50 mL), the separated organic phase was dried over $MgSO_4$ and evaporated under reduced pressure. The resulting crude was purified by flash chromatography on silica gel. Elution with cyclohexane/ethyl acetate 80/20 gave 1.94 g (45%) of 1-(pyridin-2-yl)-1-(m-tolyl)ethanol (8) as a brown oil.

$^1H$ NMR (300 MHz, $CDCl_3$): δ8.54-8.51 (m, 1H), 7.65 (dt, J=7.7, 1.7 Hz, 1H), 7.34-7.15 (m, 5H), 7.04 (d, J=7.2 Hz, 1H), 5.84 (s, 1H), 2.33 (s, 3H), 1.92 (s, 3H).

2-(1-(m-tolyl)vinyl)pyridine (9)

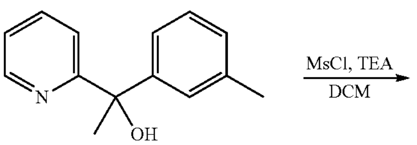

8
$C_{14}H_{15}NO$
MW: 213,28

-continued

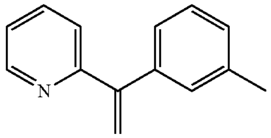

9
$C_{14}H_{13}N$
MW: 195,26

TEA (5.07 mL, 36.4 mmol) and methanesulfonyl chloride (8) (2.11 mL, 27.3 mmol) are added to a solution of 1-(pyridin-2-yl)-1-(m-tolyl)ethanol (1.94 g, 9.10 mmol) in DCM (45 mL) at 0° C. After stirring at RT overnight, the mixture was diluted with DCM (30 mL) and washed with 10% $NaHCO_3$ (25 mL) and 10% NaCl (3×25 mL). The organic phase was dried over $MgSO_4$, evaporated under reduced pressure and the resulting crude was purified by flash chromatography on silica gel. Elution with cyclohexane/ethyl acetate 90/10 gave 1.15 g (65%) of 2-(1-(m-tolyl)vinyl)pyridine (9) as a brown oil.

$^1H$ NMR (300 MHz, $CDCl_3$): δ(ddd, J=4.9, 1.8, 0.9 Hz, 1H), 7.64 (dt, J-7.7, 1.9 Hz, 1H), 7.30-7.11 (m, 6H), 5.97 (d, J=1.5 Hz, 1H), 5.59 (d, J=1.6 Hz, 1H), 2.36 (s, 3H).

2-(2-(m-tolyl) oxiran-2-yl)pyridine (10)

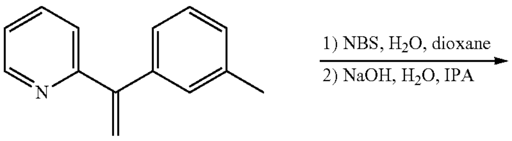

9
$C_{14}H_{13}N$
MW: 195,26

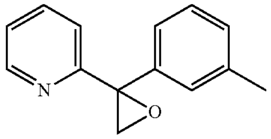

10
$C_{14}H_{13}NO$
MW: 211,26

2-(1-(m-tolyl)vinyl)pyridine (9) (1.15 g, 5.89 mmol) was dissolved in a 3:1 mixture of dioxane (36 mL) and water (12 mL). NBS (1.57 g, 8.83 mmol) was added and the mixture was stirred for 5 hours at RT. Ethyl acetate (50 mL) was added and the organic phase was washed with 10% $Na_2S_2O_5$ (30 mL) and 10% NaCl (20 mL) and evaporated under reduced pressure. The obtained residue was dissolved in IPA (40 mL), 10% NaOH (9 mL) was added and the mixture was stirred at RT for 4 hours. IPA was evaporated under reduced pressure, ethyl acetate (60 mL) was added and the organic phase was washed with 10% NaCl (20 mL), dried over $MgSO_4$ and evaporated under reduced pressure to give 1.01 g (81%) of 2-(2-(m-tolyl) oxiran-2-yl)pyridine (10) as a dark orange oil.

$^1H$ NMR (300 MHz, $CDCl_3$): δ8.62 (ddd, J=4.8, 1.8, 0.9 Hz, 1H), 7.66 (dt, J=7.8, 1.8 Hz, 1H), 7.39 (dt, J=7.9, 1.1 Hz, 1H), 7.31-7.19 (m, 4H), 7.18-7.11 (m, 1H), 3.54 (d, J=5.9 Hz, 1H), 3.26 (d, J=5.9 Hz, 1H), 2.35 (s, 3H).

2-(pyridin-2-yl)-2-(m-tolyl)ethanol (11)

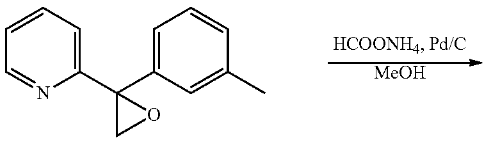

10
$C_{14}H_{13}NO$
MW: 211,26

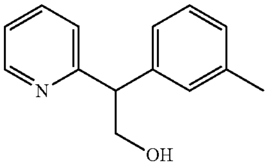

11
$C_{14}H_{15}NO$
MW: 213,28

Ammonium formate (2.98 g, 47.3 mmol) and Pd/C (KF=50%, 0.10 g) were added to a solution of 2-(2-(m-tolyl) oxiran-2-yl)pyridine (10) (1.00 g, 4.73 mmol) in anhydrous MeOH (25 mL) under nitrogen atmosphere. The mixture was refluxed for 4 hours and the solvent was evaporated under reduced pressure. The obtained residue was taken up in DCM (30 mL) and washed with 10% NaCl (10 mL). The organic phase was dried over $MgSO_4$, evaporated under reduced pressure and the resulting crude was purified by flash chromatography on silica gel. Elution with cyclohexane/ethyl acetate 70/30 gave 0.50 g (62%) of 2-(pyridin-2-yl)-2-(m-tolyl)ethanol (11) as a brown oil.

$^1H$ NMR (300 MHz, $CDCl_3$): δ8.56 (ddd, J=5.0, 1.8, 0.9 Hz, 1H), 7.58 (dt, J=7.7, 1.9 Hz, 1H), 7.24-7.14 (m, 2H), 7.09-6.97 (m, 4H), 4.41-4.22 (m, 2H), 4.05 (dd, J=10.3, 3.7 Hz, 1H), 2.32 (s, 3H).

2-(piperidin-2-yl)-2-(m-tolyl)ethanol (12)

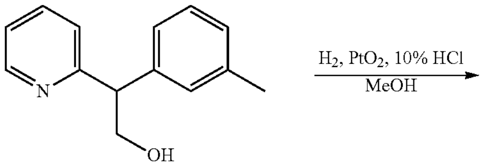

11
$C_{14}H_{15}NO$
MW: 213,28

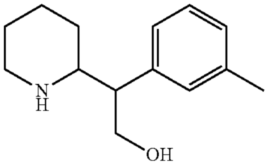

12
$C_{14}H_{21}NO$
MW: 219,32

2-(pyridin-2-yl)-2-(m-tolyl)ethanol (11) (0.62 g, 2.34 mmol) were dissolved in MeOH (50 mL) and 10% HCl (0.5 mL) and $PtO_2$ (0.10 g) were added. The mixture was vigorously stirred under 5 atm $H_2$ at RT for 4 hours and filtered on a celite/Florisil pad. The solvent was evaporated under reduced pressure to yield 0.64 g of 2-(piperidin-2-yl)-2-(m-tolyl)ethanol (12) as a brown oil. The crude was used in the next step with no further purification.

N-Boc-2-(piperidin-2-yl)-2-(m-tolyl)ethanol (13-threo and 13-erythro)

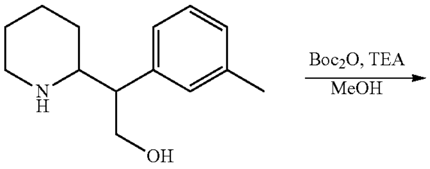

12
$C_{14}H_{21}NO$
MW: 219,32

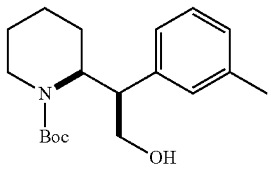

+

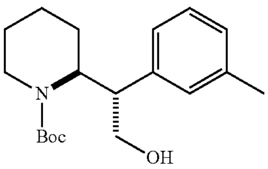

13 erythro 13 threo $C_{19}H_{29}NO_3$
MW: 319,44

A solution of $Boc_2O$ (1.31 g, 6.02 mmol) in MeOH (10 mL) was added dropwise to a solution of 2-(piperidin-2-yl)-2-(m-tolyl)ethanol (12) (0.66 g, 3.01 mmol) and TEA (0.88 mL, 6.32 mmol) in MeOH (10 mL). The mixture was refluxed for 4 hours, brought to RT and diluted with ethyl acetate (100 mL). The organic phase was washed with brine (3×30 mL), dried over $MgSO_4$, evaporated under reduced pressure and the resulting crude was purified by flash chromatography on silica gel. Elution with cyclohexane/ethyl acetate 80/20 gave 0.05 g (5%) of threo N-Boc-2-(piperidin-2-yl)-2-(m-tolyl)ethanol (13-threo) and 0.31 g (32%) of erythro N-Boc-2-(piperidin-2-yl)-2-(m-tolyl)ethanol (13-erythro) as yellow oils.

(13-threo) $^1H$ NMR (300 MHz, $CDCl_3$): δ7.23-7.02 (m, 4H), 4.70-4.58 (m, 1H), 4.10-3.96 (m, 1H), 3.65-3.48 (m, 1H), 3.40 (dd, J=10.9, 3.1 Hz, 1H), 3.11-3.00 (m, 1H), 2.90-2.74 (m, 1H), 2.34 (s, 3H), 1.50 (s, 9H), 1.64-1.28 (m, 6H). (13-erythro) $^1H$ NMR (300 MHz, $CDCl_3$): δ7.21-7.15 (m, 1H), 7.08-7.01 (m, 3H), 4.59-4.41 (m, 1H), 3.88-3.61 (m, 3H), 3.35-3.14 (m, 1H), 2.72-2.49 (m, 1H), 2.31 (s, 3H), 1.84-1.19 (m, 6H), 1.29 (s, 9H).

erythro N-Boc-2-(piperidin-2-yl)-2-(m-tolyl)acetic acid (14-erythro)

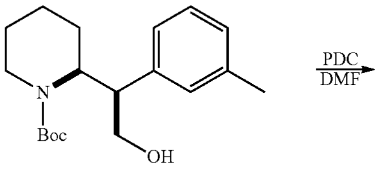

13-erythro
$C_{19}H_{29}NO_3$
MW: 319,44

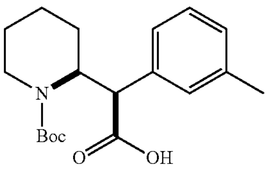

14-erythro
$C_{19}H_{27}NO_4$
MW: 333,42

Pyridinium dichromate (1.41 g, 3.76 mmol) was added to a solution of erythro N-Boc-2-(piperidin-2-yl)-2-(m-tolyl) ethanol (13-erythro) (0.30 g, 0.94 mmol) in DMF (5 mL) and the mixture was stirred at RT for 6 hours. Ethyl ether (5 mL) was added and the reaction was quenched by adding 10% HCl (2.5 mL) dropwise at 0° C. The aqueous phase was extracted with ethyl ether (3×5 mL) and the collected organic phases were extracted with 10% NaOH (3×10 mL). The collected aqueous phases were brought to pH=1 with conc. HCl and extracted with DCM (3×15 mL). The collected organic phases were dried over $MgSO_4$ and evaporated under reduced pressure to give 0.23 g (73%) of erythro N-Boc-2-(piperidin-2-yl)-2-(m-tolyl)acetic acid (14-erythro) as a greenish brown oil.

$^1H$ NMR (300 MHz, $CDCl_3$): δ7.37-7.01 (m, 4H), 5.27-4.75 (m, 1H), 4.10 (d, J=9.7 Hz, 1H), 4.22-3.62 (m, 1H), 2.81-2.59 (m, 1H), 2.34 (s, 3H), 1.90-1.53 (m, 3H), 1.55-1.05 (m, 3H), 1.27 (s, 9H).

erythro methyl 2-(piperidin-2-yl)-2-(m-tolyl)acetate hydrochloride (II-erythro)

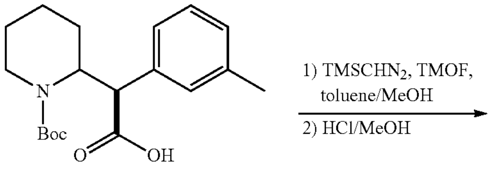

14-erythro
$C_{19}H_{27}NO_4$
MW: 333,42

-continued

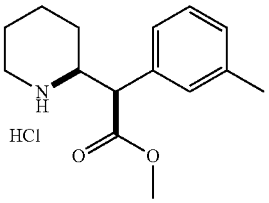

II-erythro
$C_{15}H_{22}ClNO_4$
MW: 283,79

Trimethylorthoformate (0.10 mL, 0.90 mmol) and 2M trimethylsilyldiazomethane (0.45 mL, 0.90 mmol) were added to a solution of erythro N-Boc-2-(piperidin-2-yl)-2-(m-tolyl)acetic acid (14-erythro) (0.23 g, 0.69 mmol) in toluene/MeOH (4.5 mL+4.5 mL) and the mixture was stirred at RT for 5 hours to obtain erythro methyl N-Boc-2-(piperidin-2-yl)-2-(m-tolyl)acetate (15-erythro). MeOH (5 mL) and 10% HCl (5 mL) were added and stirring was continued for additional 45 minutes. Solvents were evaporated under reduced pressure and the obtained crude was crystallized from IPE/IPA 90:10 to yield 0.10 g (51%) of erythro methyl 2-(piperidin-2-yl)-2-(m-tolyl)acetate hydrochloride (II-erythro) as a white solid (mp: 193° C. with decomposition).

$^1H$ NMR (300 MHz, $CD_3OD$): δ7.33 (t, J=7.7 Hz, 1H), 7.27-7.15 (m, 3H), 3.85 (d, J=9.2 Hz, 1H), 3.81-3.72 (m, 1H), 3.69 (s, 3H), 3.30-3.24 (m, 1H), 3.05-2.90 (m, 1H), 2.38 (s, 3H), 2.18-2.03 (m, 1H), 1.98-1.81 (m, 2H), 1.77-1.49 (m, 3H).

$^{13}C$ NMR (75 MHz, $CD_3OD$): δ171.23, 139.39, 132.36, 129.56, 129.23, 129.08, 125.59, 58.03, 54.46, 51.72, 45.57, 27.48, 21.92, 21.59, 20.05.

SCHEME 3: general procedure for the synthesis of compounds III

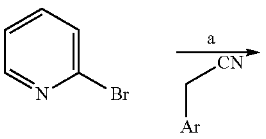

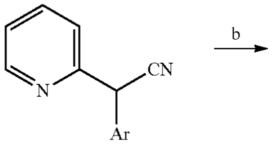

16

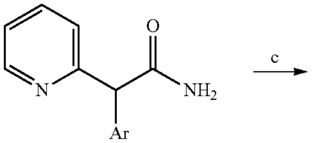

17

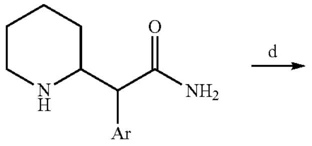

18

-continued

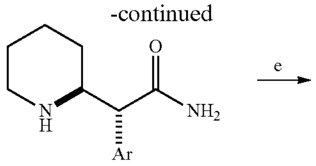

19-threo

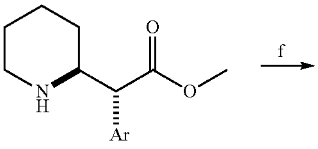

III-threo
free base

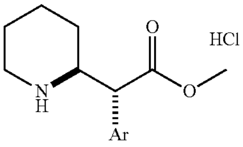

III-threo

Ar = p-methoxyphenyl

Reagents and conditions: (a) $NaNH_2$, toluene, RT; (b) $H_2SO_4$, RT: (c) $H_2$, Pd/C, AcOH, 70° C.; (d) t-BuOK, toluene, 70° C.; (e) HCl/MeOH.

A suitable phenylacetonitrile is alkylated in α-position with 2-bromopyridine, to give pyridylarylacetonitriles 16. Hydrolysis of the cyano group affords the corresponding amides 17 and subsequent catalytic hydrogenation leads to piperidyl-derivatives 18 as a mixture of threo and erythro racemates. Epimerization of amides 19 with t-BuOK completely converts the mixture in the single threo racemate. Conversion of the amide into methyl ester affords III.

Synthesis of Compound III-threo, Following SCHEME 3 2-(4-methoxyphenyl)-2-(pyridin-2-yl) acetonitrile (16)

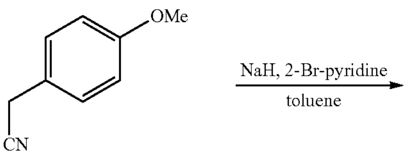

$C_9H_9NO$
MW: 147,17

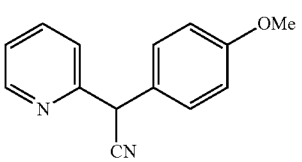

16
$C_{14}H_{12}N_2O$
MW: 224,26

4-methoxyphenylacetonitrile (4.60 mL, 34.0 mmol) and 2-bromopyridine (3.08 mL, 32.3 mmol) were added dropwise at 0° C. to a suspension of NaH (1.55 g, 64.7 mmol) in toluene (50 mL) under nitrogen atmosphere. After stirring at 80° C. overnight the reaction was quenched with the careful addition of water (20 mL). The organic phase was washed with 10% NaCl (2x20 mL), dried over $Mg_2SO_4$ and evaporated under reduced pressure. The obtained crude was crystallized from MeOH to yield 2.86 g (38%) of 2-(4-methoxyphenyl)-2-(pyridin-2-yl)acetonitrile (16) as a solid (mp: 86-89° C.).

$^1H$ NMR (300 MHz, $CDCl_3$): 8.59 (d, J=4.8 Hz, 1H), 7.69 (ddd, J=7.8, 4.8, 1.8 Hz, 1H), 7.36 (d, J=1.9 Hz, 1H), 7.38-7.33 (m, 1H), 7.33 (d, J=1.9 Hz, 1H), 7.27-7.19 (m, 1H), 6.91 (d, J=2.0 Hz, 1H), 6.88 (d, J=2.0 Hz, 1H), 5.26 (s, 1H), 3.78 (s, 3H).

2-(4-methoxyphenyl)-2-(pyridin-2-yl)acetamide

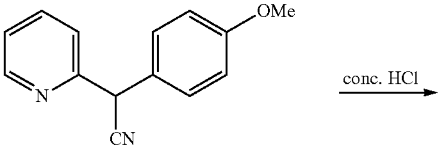

16
$C_{14}H_{12}N_2O$
MW: 224,26

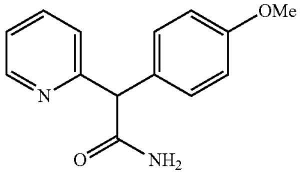

17
$C_{14}H_{14}N_2O_2$
MW: 242,27

2-(4-methoxyphenyl)-2-(pyridin-2-yl)acetonitrile (16) (1.00 g, 4.46 mmol) was dissolved in conc. HCl (10 mL) and stirred at RT for 2 hours. The mixture was poured into iced water (50 mL), basified to pH 10 with 10% NaOH and extracted with DCM (3x30 mL). The collected organic phases were dried over $Mg_2SO_4$, evaporated under reduced pressure and the obtained crude was purified by flash chromatography on silica gel. Elution with DCM/MeOH 97:3 gave 0.52 g (48%) of 2-(4-methoxyphenyl)-2-(pyridin-2-yl)acetamide (17) as a yellow oil.

$^1H$ NMR (300 MHz, $CDCl_3$) 8.60 (ddd, J=4.8, 1.8, 0.9 Hz, 1H), 7.66 (dt, J=7.7, 1.9 Hz, 1H), 7.38-7.31 (m, 2H), 7.29 (t, J=0.9 Hz, 1H), 7.20 (ddd, J=7.6, 4.9, 1.1 Hz, 1H), 6.88-6.82 (m, 2H), 4.96 (s, 1H), 3.77 (s, 3H).

2-(4-methoxyphenyl)-2-(piperidin-2-yl)acetamide (18)

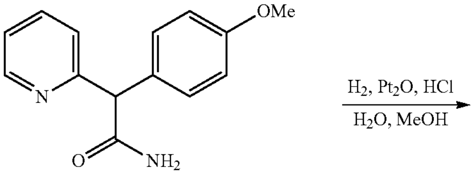

17
$C_{14}H_{14}N_2O_2$
MW: 242,27

-continued

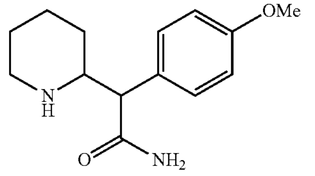

18
$C_{14}H_{20}N_2O_2$
MW: 248,32

2-(4-methoxyphenyl)-2-(pyridin-2-yl)acetamide (17) (640 mg, 2.64 mmol) was dissolved in MeOH (70 mL) and $Pt_2O$ (64 mg) and conc. HCl (0.50 mL) were added. The mixture was vigorously stirred under $H_2$ (1.5 atm) at RT for 2.5 hours and filtered on a celite/Florisil pad. The solvents were evaporated under reduced pressure and the obtained residue was taken up in water (30 mL) and basified to pH=10 with 10% NaOH. The aqueous phase was extracted with ethyl acetate (3×10 mL); the collected organic phases were dried over $Mg_2SO_4$ and evaporated under reduced pressure to yield 380 mg (56%) of a mixture of threo and erythro 2-(4-methoxyphenyl)-2-(piperidin-2-yl)acetamide (18) as a white waxy solid.

threo 2-(4-methoxyphenyl)-2-(piperidin-2-yl)acetamide (19-threo)

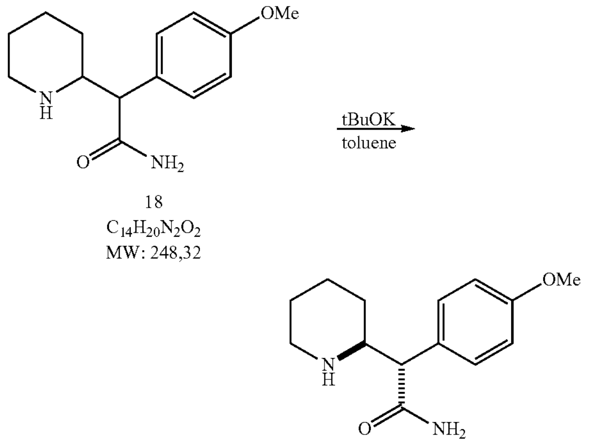

18
$C_{14}H_{20}N_2O_2$
MW: 248,32

19-threo
$C_{14}H_{20}N_2O_2$
MW: 248,32

2-(4-methoxyphenyl)-2-(piperidin-2-yl)acetamide (threo+erythro) (18) (0.38 g, 1.48 mmol) was dissolved in toluene (10 mL) and potassium tert-butylate (0.33 g, 2.96 mmol) was added under nitrogen atmosphere. After stirring at 70° C. overnight, the mixture was brought to 0° C., diluted with ethyl acetate and washed with 10% NaCl. The organic phase was dried over $Mg_2SO_4$ and evaporated under reduced pressure to yield 0.38 g (100%) of threo 2-(4-methoxyphenyl)-2-(piperidin-2-yl)acetamide (19-threo) as a white waxy solid.

$^1$H NMR (300 MHz, $CD_3OD$): δ7.26-7.21 (d, J=8.8 Hz, 2H), 6.89-6.83 (d, J=8.8 Hz, 2H), 3.76 (s, 3H), 3.27 (d, J=10.1 Hz, 1H), 3.05 (dt, J=10.5, 2.4 Hz, 1H), 3.03-2.98 (m, 1H), 2.66 (dt, J=11.8, 2.9 Hz, 1H), 1.73-1.52 (m, 2H), 1.50-1.32 (m, 1H), 1.32-1.18 (m, 2H), 1.05-0.90 (m, 1H).

threo methyl 2-(4-methoxyphenyl)-2-(piperidin-2-yl)acetate (III-threo free base)

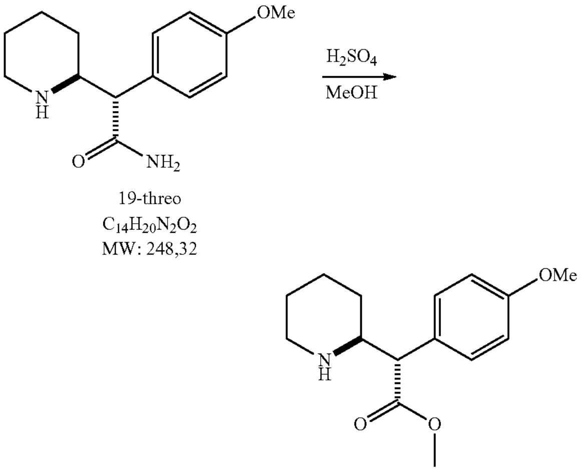

19-threo
$C_{14}H_{20}N_2O_2$
MW: 248,32

III-threo
free base
$C_{15}H_{21}NO_3$
MW: 263,33 threo 2-(4-methoxyphenyl)-2-(piperidin-2-yl)acetamide (19-threo) (0.38 g, 1.48 mmol) was dissolved in MeOH (5 mL) and conc. $H_2SO_4$ (0.5 mL) was added. The mixture was stirred at 70° C. overnight and diluted with water (20 mL) and ethyl acetate (20 mL). The aqueous phase was then basified to pH=10 with 10% NaOH and extracted with ethyl acetate (3×10 mL). The collected organic phases were dried over $Mg_2SO_4$, evaporated under reduced pressure and the obtained crude was purified by flash chromatography on silica gel. Elution with DCM/MeOH 97:3 gave 0.20 g (49%) of threo methyl 2-(4-methoxyphenyl)-2-(piperidin-2-yl)acetate (III-threo free base) as a waxy solid.

$^1$H NMR (300 MHz, $CD_3OD$): δ7.18 (d, J=8.7 Hz, 2H), 6.87 (d, J=8.7 Hz, 2H), 3.77 (s, 3H), 3.64 (s, 3H), 3.40 (d, J=10.3 Hz, 1H), 3.13 (dt, J=10.8, 2.5 Hz, 1H), 3.04-3.00 (m, 1H), 2.66 (dt, J=12.0, 2.9 Hz, 1H), 1.73-1.63 (m, 1H), 1.63-1.53 (m, 1H), 1.49-1.30 (m, 1H), 1.30-1.20 (m, 2H), 1.03-0.86 (m, 1H).

threo methyl 2-(4-methoxyphenyl)-2-(piperidin-2-yl)acetate hydrochloride (III-threo)

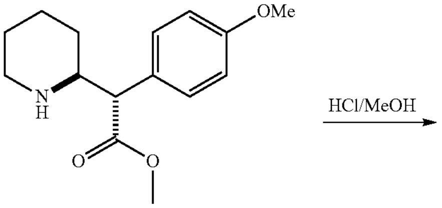

III-threo
free base
$C_{15}H_{21}NO_3$
MW: 263,33

-continued

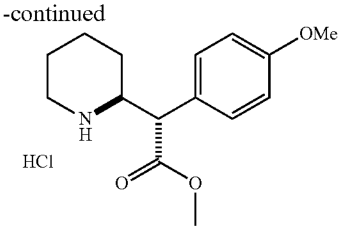

III-threo
$C_{15}H_{22}ClNO_3$
MW: 299,79 threo methyl 2-(4-methoxyphenyl)-2-(piperidin-2-yl)acetate (III-threo free base) (0.20 g, 0.76 mmol) was dissolved in MeOH (2.5 mL) and 3N HCl/MeOH (0.5 mL) was added. After stirring at RT for 5 hours, the solvent was evaporated under reduced pressure and the obtained crude was crystallized from IPE/IPA 1:2 to yield 0.11 g (48%) of threo methyl 2-(4-methoxyphenyl)-2-(piperidin-2-yl)acetate hydrochloride (III-threo) as a white solid (mp: 192.88° C.). Retention Time (HPLC)=7.69'; HPLC Purity=97%.

$^1$H NMR (300 MHz, $CD_3OD$): δ 7.19 (d, J=8.9 Hz, 2H), 6.94 (d, J=8.9 Hz, 2H), 3.79 (s, 3H), 3.77-3.72 (m, 2H), 3.72 (s, 3H), 3.45-3.41 (m, 1H), 3.41-3.37 (m, 1H), 3.08 (dt, J=12.7, 3.3 Hz, 1H), 1.94-1.75 (m, 2H), 1.75-1.39 (m, 3H), 1.38-1.22 (m, 1H).

$^{13}$C NMR (75 MHz, $CD_3OD$): δ159.98, 129.18, 125.43, 114.32, 57.94, 54.38, 53.27, 51.88, 45.24, 26.41, 22.11, 21.41.

The commercially available methyl 2-pyridylacetate is alkylated with either benzyl bromide or 4-methylbenzyl bromide to afford methyl 2-(2-pyridyl)-3-arylpropanoate derivatives 20. Catalytic hydrogenation gives 2-piperidyl derivatives 21 as a mixture of threo and erythro racemates. Protection of the piperidine nitrogen with Boc allows for the separation of racemates by column chromatography on silica gel and subsequent deprotection of the isolated threo racemate with excess 2N HCl/MeOH yields the final compounds as hydrochloride salts.

Synthesis of Compound VII-threo, Following SCHEME 4 Methyl 3-phenyl-2-(pyridin-2-yl)propanoate (20a)

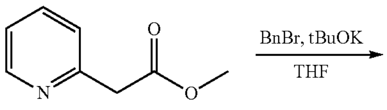

$C_8H_9NO_2$
Mw: 151,16

SCHEME 4: general procedure for the synthesis of compounds VII and IX

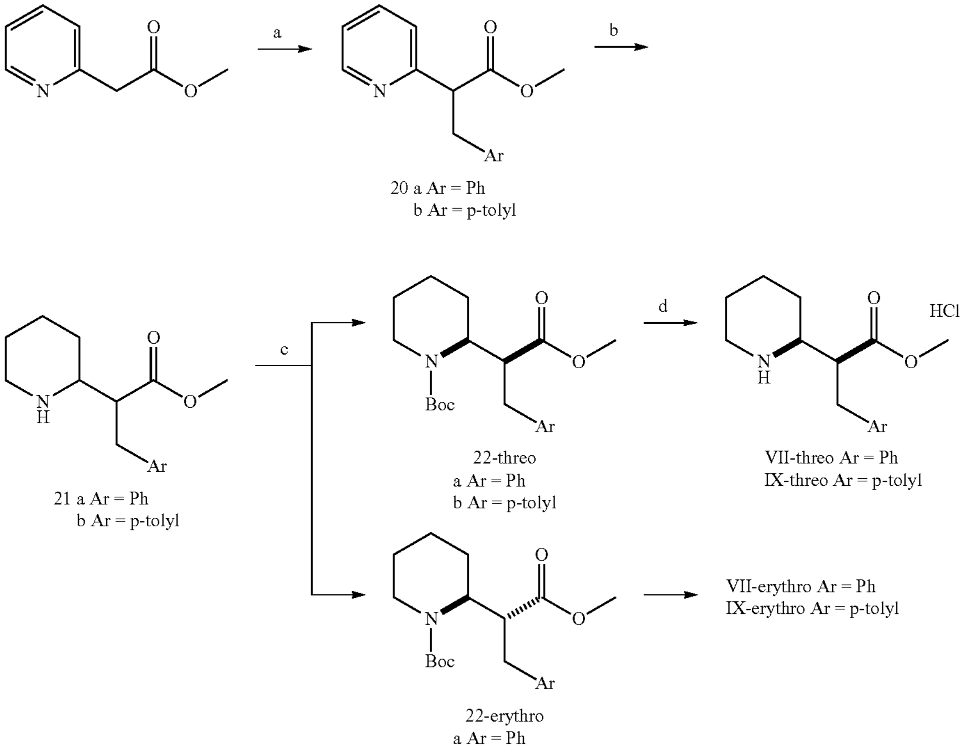

20 a Ar = Ph
b Ar = p-tolyl 21 a Ar = Ph
b Ar = p-tolyl 22-threo
a Ar = Ph
b Ar = p-tolyl VII-threo Ar = Ph
IX-threo Ar = p-tolyl 22-erythro
a Ar = Ph
b Ar = p-tolyl VII-erythro Ar = Ph
IX-erythro Ar = p-tolyl Reagents and conditions: (a) 1) t-BuOK, THF, 2) $ArCH_2Br$ (b) $H_2$ (1.5 atm), $Pt_2O$ (cat.), HCl conc., MeOH; (c) $Boc_2O$, TEA, DCM; (d) HCl/MeOH.

-continued

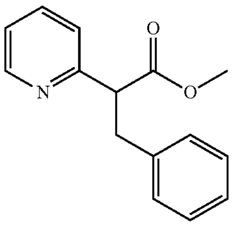

20a
$C_{15}H_{15}NO_2$
MW: 241,29

Potassium tert-butylate (3.89 g, 34.7 mmol) was added to a solution of methyl 2-(pyridin-2-yl)acetate (4.42 mL, 33.1 mmol) in anhydrous THF (165 mL) at 0° C. under nitrogen atmosphere and the mixture was stirred at the same temperature for 30 minutes. Benzyl bromide (0.79 mL, 6.62 mmol) was added and stirring was continued at RT overnight. The solvent was evaporated under reduced pressure, the residue was taken up in ethyl ether (100 mL) and washed with 10% NaCl (30 mL). The organic phase was dried over $MgSO_4$, evaporated under reduced pressure and the resulting crude was purified by flash chromatography on silica gel. Elution with cyclohexane/ethyl acetate 80/20 gave 4.56 g (57%) of methyl 3-phenyl-2-(pyridin-2-yl)propanoate (20a) as a light-yellow oil.

$^1H$ NMR (300 MHz, $CDCl_3$) 0 8.59 (ddd, J=4.9, 1.8, 0.9 Hz, 1H), 7.59 (dt, J=7.7, 1.8 Hz, 1H), 7.24-7.10 (m, 7H), 4.14-4.08 (m, 1H), 3.64 (s, 3H), 3.46 (dd, J=13.8, 8.2 Hz, 1H), 3.24 (dd, J=13.8, 7.4 Hz, 1H).

Methyl 3-phenyl-2-(piperidin-2-yl)propanoate (21a)

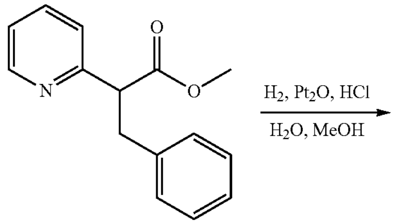

20a
$C_{15}H_{15}NO_2$
MW: 241,29

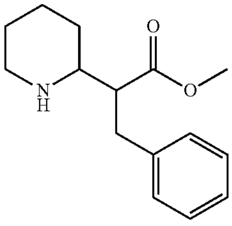

21a
$C_{15}H_{21}NO_2$
MW: 247,33

Methyl 3-phenyl-2-(pyridin-2-yl)propanoate (20a) (0.70 g, 2.90 mmol) was dissolved in MeOH (30 mL) and $Pt_2O$ (0.07 g) and conc. HCl (0.2 mL) were added. The mixture was vigorously stirred under $H_2$ (1.5 atm) at RT for 5 hours and filtered on a celite/Florisil pad. The solvents were evaporated under reduced pressure and the obtained residue was taken up in ethyl acetate (30 mL) and washed with 10% NaOH (10 mL) and 10% EDTA (10 mL). The organic phase was dried over $MgSO_4$, evaporated under reduced pressure to yield 0.60 g (73%) of methyl 3-phenyl-2-(piperidin-2-yl) propanoate (21a) as a yellow oil.

$^1H$ NMR (300 MHz, $CDCl_3$): δ7.30-7.15 (m, 5H), 3.56 (s, 3H), 3.23 (t, J=12.8 Hz, 1H), 3.13-2.92 (m, 2H), 2.92-2.77 (m, 1H), 2.73-2.61 (m, 1H), 1.92-1.78 (m, 1H), 1.75-1.31 (m, 5H).

N-Boc methyl 3-phenyl-2-(piperidin-2-yl)propanoate (22a-threo and 22a-erythro)

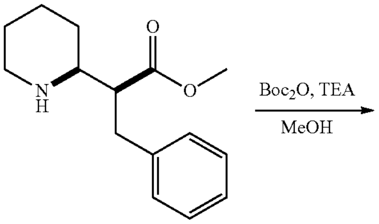

21a
$C_{15}H_{21}NO_2$
MW: 247,33

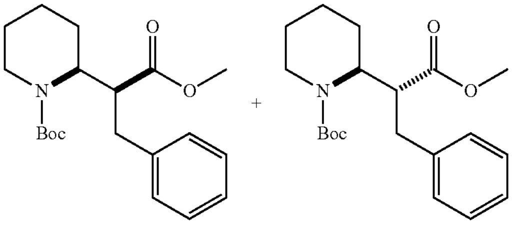

22a-threo 22a-erythro $C_{20}H_{29}NO_4$
MW: 347,45

Methyl 3-phenyl-2-(piperidin-2-yl)propanoate (21a) (1.08 g, 4.37 mmol) and TEA (1.28 mL, 9.17 mmol) were dissolved in MeOH (20 mL) and a solution of $Boc_2O$ (1.90 g, 8.73 mmol) in MeOH (10 mL) was added dropwise. The mixture was refluxed for 2 hours and the solvent was evaporated under reduced pressure. The obtained residue was taken up in ethyl acetate (20 mL) and washed with 10% NaCl (2×10 mL). The organic phase was dried over $MgSO_4$, evaporated under reduced pressure and the resulting crude was purified by flash chromatography on silica gel. Elution with cyclohexane/ethyl acetate 100/0 to 85/15 gave 0.10 g (6%) of threo N-Boc methyl 3-phenyl-2-(piperidin-2-yl) propanoate (22a-threo) and 0.10 g (6%) of erythro N-Boc methyl 3-phenyl-2-(piperidin-2-yl)propanoate (22a-erythro) as colorless oils.

(22a-threo) $^1H$ NMR (300 MHz, $CDCl_3$): δ7.31-7.23 (m, 2H), 7.23-7.13 (m, 3H), 4.56-4.46 (m, 1H), 4.06-3.92 (m, 1H), 3.49 (s, 3H), 3.24 (dt, J=11.1, 4.2 Hz, 1H), 3.01-2.85 (m, 2H), 2.83-2.72 (m, 1H), 1.92-1.79 (m, 1H), 1.69-1.53 (m, 5H), 1.45 (s, 9H).

(22a-erythro) $^1H$ NMR (300 MHz, $CD_3OD$): δ7.28-7.21 (m, 2H), 7.21-7.16 (m, 1H), 7.14-7.09 (m, 2H), 4.56-4.41 (m, 1H), 4.14-3.97 (m, 1H), 3.49 (s, 3H), 3.24 (dd, J=11.2, 4.4 Hz, 1H), 2.94-2.73 (m, 1H), 2.79 (dd, J=13.5, 11.1 Hz, 1H), 2.67 (dd, J=13.5, 4.3 Hz, 1H), 1.76-1.41 (m, 6H), 1.50 (s, 9H).

threo methyl 3-phenyl-2-(piperidin-2-yl)propanoate hydrochloride (VII-threo)

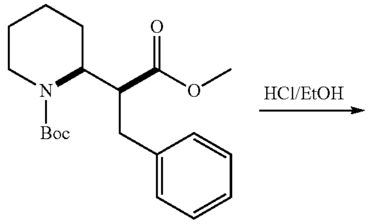

22a-threo
$C_{20}H_{29}NO_4$
MW: 347,45

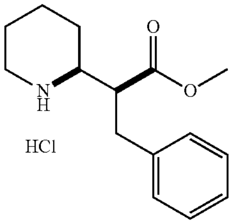

VII-threo
$C_{15}H_{22}ClNO2$
MW: 283,79 threo N-Boc methyl 3-phenyl-2-(piperidin-2-yl)propanoate (22a-threo) (250 mg, 0.72 mmol) was dissolved in excess 3N HCl/EtOH and stirred at RT overnight. The solvent was evaporated under reduced pressure and the obtained residue was slurried in cold diethyl ether to give 200 mg (100%) of superior methyl 3-phenyl-2-(piperidin-2-yl)propanoate hydrochloride (VII-threo) as a white solid (mp: 161.90° C.). Retention Time (HPLC)=8.06'; HPLC Purity=94%.

$^1H$ NMR (300 MHz, $CD_3OD$): δ7.33-7.28 (m, 2H), 7.25-7.19 (m, 3H), 3.61 (s, 3H), 3.48-3.38 (m, 1H), 3.37-3.27 (m, 1H), 3.15-3.05 (m, 1H), 3.05-2.94 (m, 3H), 2.06-1.83 (m, 3H), 1.83-1.63 (m, 1H), 1.63-1.49 (m, 2H).

$^{13}C$ NMR (75 MHz, $CD_3OD$): δ172.53, 137.26, 128.46, 128.27, 126.64, 57.94, 51.28, 50.57, 45.76, 34.28, 26.88, 21.87, 21.80.

SCHEME 5: general procedure for the synthesis of compounds VIII

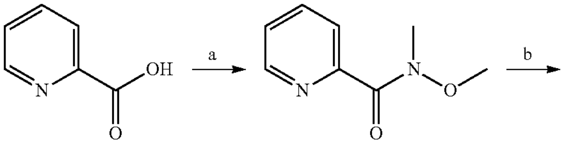

23

-continued

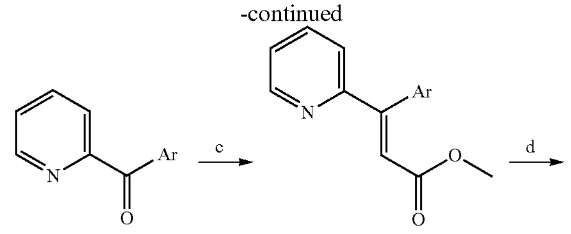

24

25 E/Z

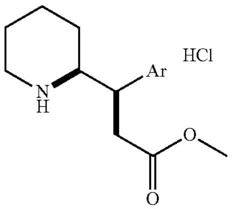

VIII-erytho

Ar = Ph

Reagents and conditions: (a) N,O-dimethylhydroxylamine hydrochloride, CDI, DCM; (b) phenyllitium, THF, -20° C.; (c) diethymethylphosphonacetate, NaH; (d) $H_2$ (1.5 atm), $Pt_2O$ (cat.), HCl conc., MeOH.

In the synthesis of VIII commercially available 2-picolinic acid is converted into the corresponding Weinreb amide 23 and treated with phenyllithium to give biarylketone 24. Wittig-Horner reaction with diethylmethylphosphonacetate affords 25 as a mixture of E and Z isomers, that are not separated and undergo catalytic hydrogenation to reduce both the olefin and the pyridyl ring.

Synthesis of compound VIII-erythro, Following SCHEME 5 N-methoxy-N-methylpicolinamide (23)

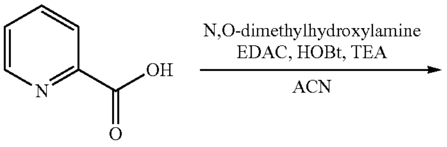

$C_6H_5NO_2$
MW: 123,11

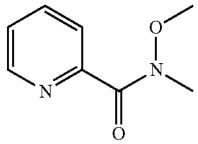

23
$C_8H_{10}N_2O_2$
MW: 166,18

TEA (5.94 mL, 42.6 mmol) was added dropwise to a suspension of picolinic acid (5.00 g, 40.6 mmol), N,O-dimethylhydroxylamine (4.16 g, 42.6 mmol), EDAC (9.34 g, 48.7 mmol) and HOBt (1.87 g, 12.2 mmol) in ACN (50 mL) under nitrogen atmosphere and the mixture was stirred at RT for 3 days. Saturated NaCl (60 mL) was added and ACN was evaporated under reduced pressure. The aqueous phase was extracted with ethyl acetate (3×20 mL), the collected organic phases were washed with 10% $NaHCO_3$ (20 mL), dried over $MgSO_4$ and evaporated under reduced pressure to yield 5.99 g (89%) of N-methoxy-N-methylpicolinamide (23) as a yellow oil.

$^1$H NMR (300 MHz; $CDCl_3$): δ 8.61 (m, 1H), 7.79-7.76 (m, 1H), 7.70-7.59 (m, 1H), 7.39-7.32 (m, 1H), 3.74 (s, 3H), 3.2 (s, 3H).

Phenyl(pyridin-2-yl)methanone (24)

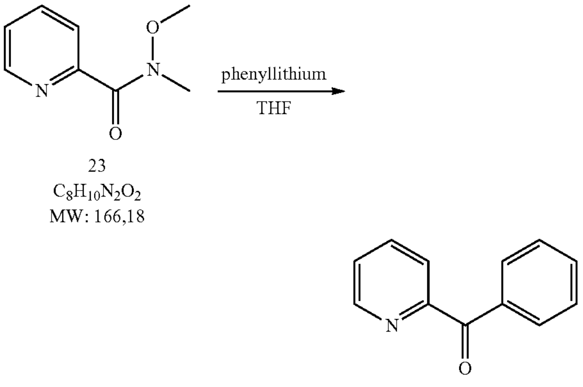

23
$C_8H_{10}N_2O_2$
MW: 166,18

24
$C_{12}H_9NO$
MW: 183,21

1.9M phenyllithium (4.90 mL, 9.41 mmol) was added to a solution of N-methoxy-N-methylpicolinamide (23) (0.98 g, 5.88 mmol) in anhydrous THF (10 mL) at −20° C. under nitrogen atmosphere and stirred for 2 hours. The reaction was quenched with the dropwise addition of 2N HCl/MeOH (5.88 mL, 11.8 mmol) at the same temperature. The solvent was evaporated under reduced pressure and the obtained residue was dissolved in ethyl acetate (60 mL). The organic phase was extracted with 10% HCl (3×20 mL) and the collected aqueous phases were basified with NaOH pellets and extracted with ethyl acetate (3×20 mL). The collected organic phases were dried over $MgSO_4$ and evaporated under reduced pressure to yield 0.91 g (84%) of phenyl (pyridin-2-yl)methanone (24) as a yellow oil.

$^1$H NMR (300 MHz; $CDCl_3$): 0 8.79-8.66 (m, 1H), 8.05 (ddd, J=6.9, 6.0, 1.1 Hz, 3H), 7.95-7.85 (m, 1H), 7.66-7.55 (m, 1H), 7.53-7.44 (m, 3H).

Trimethyl Phosphonoacetate

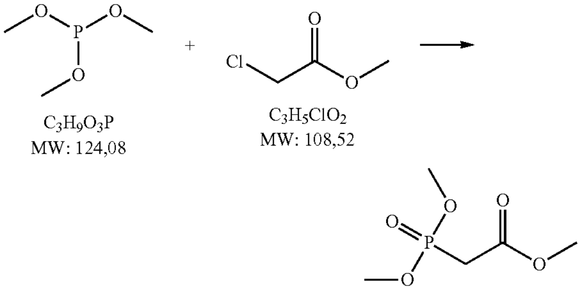

$C_3H_9O_3P$
MW: 124,08

$C_3H_5ClO_2$
MW: 108,52

$C_5H_{11}O_5P$
MW: 182,11

Trimethyl phosphite (4.75 mL, 40.3 mmol) and methyl chloroacetate (2.05 mL, 33.6 mmol) were stirred at 100° C. for 3 days. The mixture was then diluted with ethyl acetate (60 mL) and washed with water (2×20 mL) and 10% NaCl (20 mL). The organic phase was dried over $MgSO_4$ and carefully evaporated under reduced pressure to yield 2.71 g (44%) of trimethyl phosphonoacetate as a light-yellow oil.

$^1$H NMR (300 MHz, $CDCl_3$): δ3.81 (d, J=11.3 Hz, 6H), 3.75 (s, 3H), 3.02 (d, J=0.9 Hz, 1H), 2.95 (d, J=0.9 Hz, 1H).

(E,Z)-methyl 3-phenyl-3-(pyridin-2-yl)acrylate

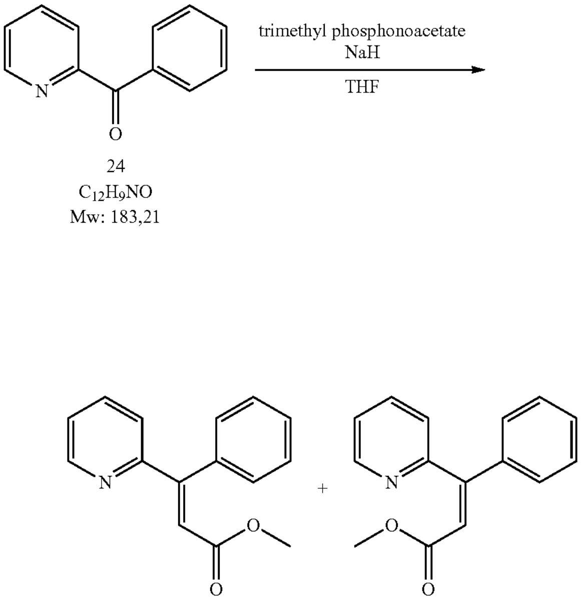

24
$C_{12}H_9NO$
Mw: 183,21

25 E e Z
$C_{15}H_{13}NO_2$
MW: 239,27

A solution of trimethyl phosphonoacetate (4.73 g, 25.9 mmol) in anhydrous THF (10 mL) was added dropwise to a suspension of NaH (0.62 g, 25.9 mmol) in anhydrous THF (10 mL) at 0° C. under nitrogen atmosphere. After stirring for 1 hour, a solution phenyl(pyridin-2-yl)methanone (24) (4.33 g, 23.6 mmol) in anhydrous THF (20 mL) was added and stirring was continued for 3 days. The reaction was quenched with the addition of 10% HCl (15 mL) and THF was evaporated under reduced pressure. The mixture was then diluted with 10% HCl (10 mL) and water (25 mL) and washed with ethyl ether (10 mL). The aqueous phase was basified with NaOH pellets and extracted with ethyl acetate (3×20 mL). The collected organic phases were dried over $MgSO_4$, evaporated under reduced pressure and the resulting crude was purified by flash chromatography on silica gel. Elution with toluene/ethyl acetate 95/5 gave 1.18 g (21%) of (Z)-methyl 3-phenyl-3-(pyridin-2-yl)acrylate (25-Z) and 1.00 g (18%) of (E)-methyl 3-phenyl-3-(pyridin-2-yl)acrylate (25-E) as light yellow oils.

E isomer $^1$H NMR (300 MHz, $CDCl_3$): δ8.68-8.65 (m, 1H), 7.58 (dt, J=7.7, 1.9 Hz, 1H), 7.44-7.39 (m, 3H), 7.28-7.22 (m, 3H), 7.18 (s, 1H), 7.00 (dt, J=8.0, 1.0 Hz, 1H), 3.61 (s, 3H).

Z isomer $^1$H NMR (300 MHz, $CDCl_3$): δ8.69 (dd, J=4.1, 1.1 Hz, 1H), 7.75 (td, J=7.7, 1.1 Hz, 1H), 7.46-7.13 (m, 7H), 6.49 (s, 1H), 3.61 (s, 3H).

erythro methyl 3-phenyl-3-(piperidin-2-yl)propanoate hydrochloride (VIII-erythro)

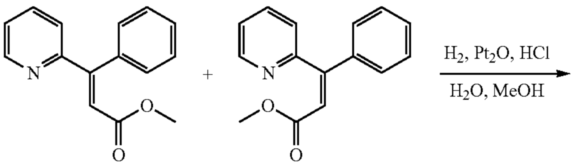

25 E e Z
$C_{15}H_{13}NO_2$
MW: 239,27

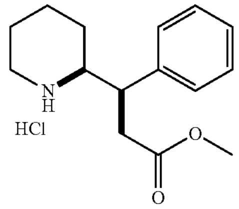

VIII-erythro
$C_{15}H_{22}Cl_2NO_2$
MW: 319.25

(E,Z)-methyl 3-phenyl-3-(pyridin-2-yl)acrylate (25-E/Z) (2.20 g, 9.20 mmol) was dissolved in MeOH (70 mL) and $Pt_2O$ (0.11 g) and conc. HCl (0.90 mL) were added. The mixture was vigorously stirred under $H_2$ (1.5 atm) at RT for 4 hours and filtered on a celite/Florisil pad. The solvents were evaporated under reduced pressure and the obtained crude was crystallized from IPE to yield 2.57 g (98%) of erythro methyl 3-phenyl-3-(piperidin-2-yl)propanoate (VIII-erythro) as a white solid (mp: 171.27° C.).

$^1H$ NMR (300 MHz, $CD_3OD$): δ7.25-7.20 (m, 5H), 4.48-4.40 (m, 1H), 3.85-3.73 (m, 1H), 3.65 (ddd, J=11.1, 10.2, 5.0 Hz, 1H), 3.47 (s, 3H), 2.92-2.81 (m, 1H), 2.76 (dd, J=15.2, 4.9 Hz, 1H), 2.61 (dd, J=15.2, 10.0 Hz, 1H), 1.95-1.81 (m, 1H), 1.81-1.71 (m, 1H), 1.72-1.57 (m, 3H), 1.47-1.28 (m, 1H), 1.21 (s, 9H).

SCHEME 6: general procedure for the synthesis of compounds X

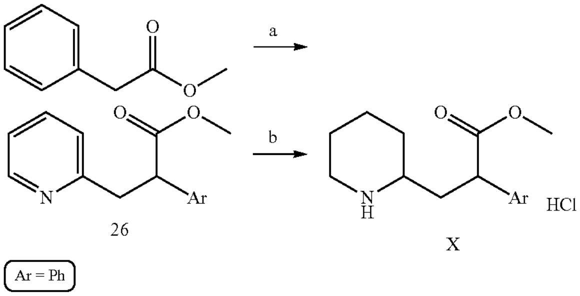

26

X

Reagents and conditions: (a) 2-(bromomethyl)pyridine hydrobromide, t-BuOK, THF (b) $H_2$ (1.5 atm), $Pt_2O$ (cat.), HCl conc., MeOH.

X is synthesized starting with the alkylation of commercially available methyl phenylacetate with 2-(bromomethyl) pyridine to give methyl 3-(2-pyridyl)-2-phenylpropionate 26. Reduction via catalytic hydrogenation gives 3-piperidyl derivative X as a mixture of threo and erythro racemates.

Synthesis of Compound X, Following SCHEME 6 Methyl 2-phenyl-3-(pyridin-2-yl)propanoate (26)

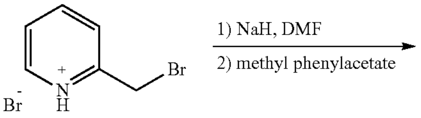

$C_6H_7Br_2N$
MW: 252,93

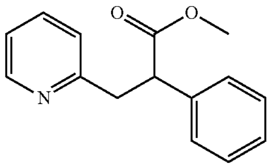

26
$C_{15}H_{15}NO_2$
MW: 241,29

A solution of 2-(bromomethyl)pyridine hydrobromide (8.84 g, 35.0 mmol) in DMF (50 mL) and a solution of methyl phenylacetate (5.00 g, 33.3 mmol) in DMF (50 mL) were added dropwise to a suspension of NaH (1.64 g, 68.2 mmol) in DMF (30 mL) at 0° C. The mixture was stirred 4 hours at RT and the solvent was evaporated under reduced pressure. The obtained residue was taken up in ethyl acetate (75 mL) and washed with 10% NaCl (4×25 mL). The organic phase was dried over $MgSO_4$, evaporated under reduced pressure and the resulting crude was purified by flash chromatography on silica gel. Elution with cyclohexane/ethyl acetate 70/30 gave 5.40 g (67%) of methyl 2-phenyl-3-(pyridin-2-yl)propanoate (26) as a light yellow oil.

$^1H$ NMR (300 MHz, $CDCl_3$): δ8.55-8.51 (m, 1H), 7.51 (td, J=7.7, 1.8 Hz, 1H), 7.36-7.22 (m, 5H), 7.11-7.07 (m, 1H), 7.05 (d, J=7.8 Hz, 1H), 4.28 (dd, J=9.2, 6.3 Hz, 1H), 3.62 (dd, J=9.4 Hz, 1H), 3.61 (s, 3H), 3.16 (dd, J=14.2, 6.3 Hz, 1H).

Methyl 2-phenyl-3-(piperidin-2-yl)propanoate (X)

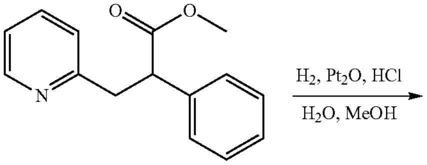

26
$C_{15}H_{15}NO_2$
MW: 241,29

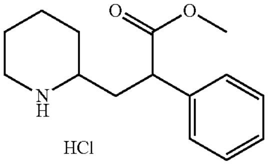

X
$C_{15}H_{22}ClNO_2$
MW: 283,79

Methyl 2-phenyl-3-(pyridin-2-yl)propanoate (26) (5.40 g, 22.4 mmol) was dissolved in MeOH (100 mL) and $Pt_2O$ (0.42 g) and conc. HCl (2.0 mL) were added. The mixture was vigorously stirred under $H_2$ (1.5 atm) at RT for 4 hours and filtered on a celite/Florisil pad. The solvents were evaporated under reduced pressure to yield 6.16 g (97%) of a mixture of diasteroisomers of methyl 2-phenyl-3-(piperidin-2-yl)propanoate (X) as a white solid.

Evaluation of the Capacity of the Different Methylphenidate Derivatives to Stimulate the Functional Interaction Between Alpha-Synuclein and Synapsin III in Neuronal-Like Cells Exhibiting Alpha-Synuclein/Synapsin III Co-Aggregates The ability of the different compound to stimulate alpha-synuclein/Synapsin III interaction was evaluated by acceptor photobleaching FRET or FLIM in neuronal-like cells. In particular, we used neuronal-differentiated SK—N—SH neuroblastoma cells transiently transfected with red fluorescent protein (RFP)-tagged human wild type alpha-synuclein and green fluorescent protein (GFP)-tagged the human 63 kDa Synapsin III isoform.

Acceptor Photobleaching Fluorescence Resonance Energy Transfer (FRET) Studies

Acceptor photobleaching FRET microscopy allows an accurate evaluation of protein-protein interaction through the measurement of FRET efficiency. This parameter is indicative of the increase of donor fluorescence after complete photobleaching of the acceptor fluorescence, within a FRET pair of fluorophores (where the emission wavelength of a donor falls within the excitation wavelength of an acceptor). Since FRET efficiency is detectable only when the two fluorophores are sufficiently close to ensure that their linked proteins are interacting, the molecular proximity of these latter results strictly dependent on this parameter[36,37]. We thus measured donor (GFP-Synapsin III) fluorescence after the complete photobleaching of the acceptor (RFP-alpha-synuclein) in the cells that were treated for 15 min with MPH, I-threo, IV-threo, V-threo or VI-threo at 10 μM concentration. Human neuroblastoma SK—N—SH cells were grown in complete medium comprising Dulbecco's modified Eagle's medium with 1000 mg glucose/l supplemented with 10% heat-inactivated fetal bovine serum, 100 μg/ml penicillin and 100 μg/ml streptomycin. Cells were maintained at 37° C. under a humidified atmosphere of 5% CO2 and 95% O2. For FRET studies, SK—N—SH cells were seeded onto poli-D-lysine-coated 13 mm glass coverslips in 24-well plates (15000 cells per coverslip) and were maintained in differentiation medium for ten days by daily adding 10 μM retinoic acid to the medium. At day 7, cells were transiently transfected with pGFP-human Synapsin III (transducing human green fluorescent protein (GFP)-tagged Synapsin III and pCMV6-RFP-alpha-synuclein (transducing red fluorescent protein (RFP)-tagged alpha-synuclein) constructs, by using Lipofectamine 3000, according to the manufacturer's instructions. pCMV6-RFP-alpha-synuclein single-transfected cells were used as negative controls during the FRET experiments. Three days after transfection, cells were treated for 15 min with vehicle (normal saline 0.9%-control), 10 μM MPH (d-threo), 10 μM I-threo, 10 μM IV-threo, 10 μM I-erythro, 10 μM V-threo or 10 μM VI-threo, then immediately fixed with Immunofix for 15 min and subsequently mounted on glass slides. Fixed cells were analyzed by means of a Zeiss confocal laser microscope LSM 880 (Carl Zeiss) with the laser set on A=488-543. After identifying double positive cells three-to-six regions of interest (ROI) were analyzed for 4 series. Two images of basal condition (Pre-bleaching) were acquired before bleaching the RFP acceptor fluorophore with laser 543 set at 65% power. Then, other two images were acquired after the bleaching (Post-bleaching). The FRET efficiency (intended as the GFP recovery after RFP photobleaching) was measured by using Zen black software (Carl Zeiss). The average intensity of the background (outside the cell) was subtracted from the average intensity of the ROI and all the FRET values resulting from the different ROI were used for statistical analysis.

Analysis of the acceptor photobleaching FRET experiments showed (FIG. 1) that MPH and VI-threo treatment induced a comparable statistically significant increase (+3.4%, $P<0.05$ and +3.4%, $P<0.05$, respectively. One-way ANOVA+Newman-Keuls multiple comparison test) in the interaction between alpha-synuclein and Synapsin III measured at % FRET efficiency changes when compared to control untreated neuronally differentiated SK—N—SH cells. Remarkably, I-threo treatment was found to increase of three times the ability of alpha-synuclein to interact with Synapsin III with respect of the untreated cells (+8.8, $P<0.001$, One-way ANOVA+Newman-Keuls multiple comparison test) and almost double the effect of MPH and VI-threo (+5.5%, $P<0.05$ and +5.2%, $P<0.05$, respectively. One-way ANOVA+Newman-Keuls multiple comparison test). IV-threo, I-erythro and V-threo were not able to stimulate alpha-synuclein/Synapsin III interaction.

Live Imaging and Fluorescence Lifetime Microscopy (FLIM):

It was needed to confirm the observation that I-threo is able to stimulate alpha-synuclein/Synapsin III interaction more efficiently that MPH by using FLIM, a technique that measures GFP donor fluorescence lifetime in absence and in presence of the RFP acceptor and when energy transfer between donor and acceptor occurs, donor lifetime is decreased. The comparison of the lifetimes of the donor alone and in presence of the acceptor allows for precise and concentration-independent measurements of FRET efficiency. Fluorescence lifetime is defined as the average time that a fluorophore spends in the excited state after the absorption of light, prior to returning to the ground state by emitting a photon. Donor fluorescence lifetime is decreased when FRET occurs between the fluorophore pair. The comparison of the lifetimes of the donor alone and in presence of the acceptor allows for precise and concentration-independent measurements of FRET efficiency (Ishikawa-Ankerhold, H. C. et al. Molecules (Basel, Switzerland) 2012, 17, 4047-4132). Human neuroblastoma SK—N—SH cells were grown in complete medium comprising Dulbecco's modified Eagle's medium with 1000 mg glucose/l supplemented with 10% heat-inactivated fetal bovine serum, 100 μg/ml penicillin and 100 μg/ml streptomycin. Cells were maintained at 37° C. under a humidified atmosphere of 5% CO2 and 95% 02. For FRET/FLIM studies, SK—N—SH cells were seeded onto poli-D-lysine-coat 1.7 cm2 glass chamber (15000 cells per well) and were maintained in differentiation medium for ten days by daily adding 10 μM retinoic acid to the medium. At day 7, cells were transiently transfected with pGFP-human Synapsin III (transducing human green fluorescent protein (GFP)-tagged Synapsin III and pCMV6-RFP-alpha-synuclein (transducing RFP-tagged alpha-synuclein) constructs, by using Lipofectamine 3000, according to the manufacturer's instructions. pCMV6-RFP-alpha-synuclein single-transfected cells were used as negative controls during the FRET experiments. Three days after transfection, cells were placed under a confocal Zeiss LSM 880 microscope, operated with ZEN software (Zeiss), equipped with an environmental chamber that maintains the temperature at 37° C. and with a supply of humidified 5% CO2 to the cells. Cells were imaged with 488 and 594 nm confocal lasers for GFP and RFP, respectively, with a 63× oil immersion objective, immediately prior to FLIM) of the same field of view. Cells were treated with vehicle (normal saline 0.9%-control), 10 μM MPH (d-threo), 10 μM I-threo, 10 μM I-erythro or 10 μM VI-threo and the image were recorded 15 min after the treatment. The time-domain FLIM was measured using a Time-Correlated Single Photon Counting (TCSPC) (PicoQuant) operated with SymPhoTime 64 software (PicoQuant). The two-photon laser (Chameleon) integrated with a Zeiss 880 microscope and operated with ZEN software generated the required pulsed illumination with a repetition rate of 80 MHz and pulse width of 500 fs. For GFP excitation, the wavelength was set to 860 nm. The images of GFP fluorescence generated in ZEN software were stored and processed with SymPhoTime 64. The mean fluorescence intensities within cell body were determined using the ROI tool in SymPhoTime 64. The mean intensity of the background measured in several regions that did not contain cells was further subtracted from the fluorescence intensity data. The fluorescence lifetime analysis was performed in the SymPhoTime 64 software within the cell body, automatically recognized by the software as ROI 0. Individual photon arrivals were detected using a SPAD detector and events were recorded by a PicoHarp 300 TCSPC module. Mono and bi exponential fittings were obtained for GFP alone and in the presence of RFP, respectively. The samples of GFP alone were performed under identical conditions in the absence of RFP. The percentage FLIM-FRET efficiency was calculated as: 100×[1−(lifetime of donor with FRET/lifetime of donor without FRET)]. For lifetime analysis, fifteen cells were recorded for each condition, included GFP alone.

Figure 2:
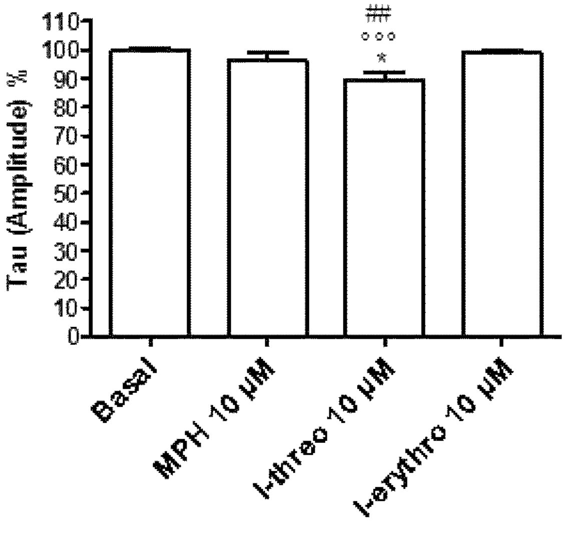
FIG. 2 shows FLIM-FRET efficiency, expressed donor lifetime (Tau-Amplitude) upon MPH, I-threo and its erythro isomer I-erythro treatment. The experiment again confirms that only I-threo is able to promote alpha-synuclein/synapsin III interaction. (°°° $P<0.001$ vs. Basal; ##$P<0.01$ vs. MPH 10 μM; One-way ANOVA+Newman-Keuls' post comparison test).

Again, it was confirmed (FIG. 2) that the cells treated with I-threo exhibited a rate of alpha-synuclein/Synapsin III interaction estimated by the % decrease of tau amplitude that was significantly higher than that observed by MPH treated (##-8.4%, P<0.01, respectively. One-way ANOVA+Newman-Keuls multiple comparison test) and untreated cells (°°°-11.95%, P<0.001, respectively. One-way ANOVA+Newman-Keuls multiple comparison test). Interestingly, I-erythro, the erythro isomer of I-threo, did not stimulate alpha-synuclein/Synapsin III interaction as previously observed by FRET.

Immunocytochemistry:

Human neuroblastoma SK—N—SH full length (fl) alpha-synuclein stable clones were seeded onto poly-D-lysine-coated glass coverslides in 24-well plates and were grown in complete medium comprising Dulbecco's modified Eagle's medium with 1000 mg glucose/l supplemented with 10% heat-inactivated fetal bovine serum, 100 μg/ml penicillin and 100 μg/ml streptomycin. Cells were maintained at 37° C. under a humidified atmosphere of 5% CO2 and 95% 02. At 80% confluence, cells underwent glucose deprivation (GD) in order to induce alpha-synuclein aggregation (Bellucci, A.; et al. *Journal of neurochemistry* 2008, 106, 560-577). Briefly, GD was performed through an incubation of the cells with Hank's balanced salt solution supplemented with 2 mM glutamine and 10% heat-inactivated fetal bovine serum, for 1 h at 37° C. Then this medium was removed and replaced either with complete medium or with complete medium plus 10 μM MPH (d-threo), 10 μM I-threo or 10 μM VI-threo. After 24 h of treatment, cells were fixed by incubating for 15 min in 4% paraformaldehyde with 4% sucrose in 1 M PBS, pH 7.4. The fixed cells were then stored in PBS-containing 0.05% sodium azide. Slides were incubated for 1 h at room temperature in blocking solution [2% w/v bovine serum albumin (BSA) plus 3% v/v normal goat serum in PBS], then overnight at 4° C. with the primary antibody (Syn211 antibody against alpha-synuclein) at the optimal working dilution. On the following day, cells were incubated for 1 h at room temperature with the Cy3-conjugated secondary antibody diluted in 0.1% Triton X-100 PBS plus BSA 1 mg/ml. Finally, cell nuclei were counterstained with Hoechst 33258 dye, and the coverslips were mounted onto glass slides using Vectashield.

Figure 3:
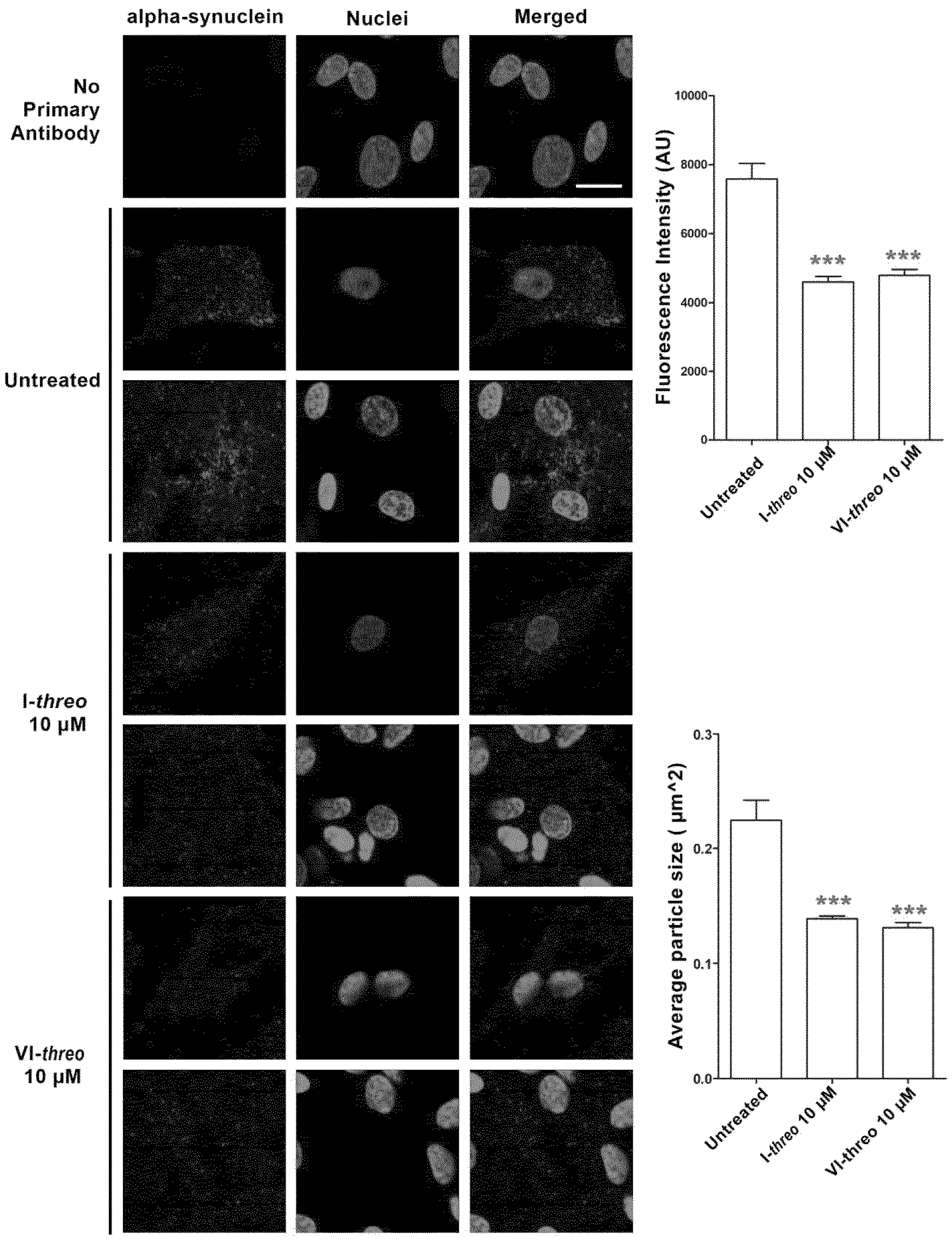
FIG. 3 shows the effect of I-threo and VI-threo treatment on SK—N—SH cells overexpressing alpha-synuclein exposed to glucose deprivation. Both the compounds are able to significantly reduce alpha-synuclein aggregation in vitro (*** P<0.001 vs. untreated; One-way ANOVA+Newman-Keuls' post comparison test).

It was found (FIG. 3) that both I-threo and VI-threo treatment could significantly reduce the formation of alpha-synuclein inclusions after GD as detected by immunofluorescence intensity and average alpha-synuclein-positive particle size. This set of preliminary results shows a reduction in the formation of alpha-synuclein aggregates (white arrows) induced by GD in neuroblastoma cells treated with MPH compared to non-treated (NT) cells. Interestingly, after treatment with I-threo and VI-threo no aggregates were observed, suggesting a positive effect of these compounds on alpha-synuclein misfolding and supporting a neuroprotective effect. It was then assessed the ability of MPH at 100 nM or I-threo, VI-threo at 50 and 100 nM concentration to prevent alpha-synuclein aggregation in primary mouse midbrain neurons exposed to GD.

Figure 4:
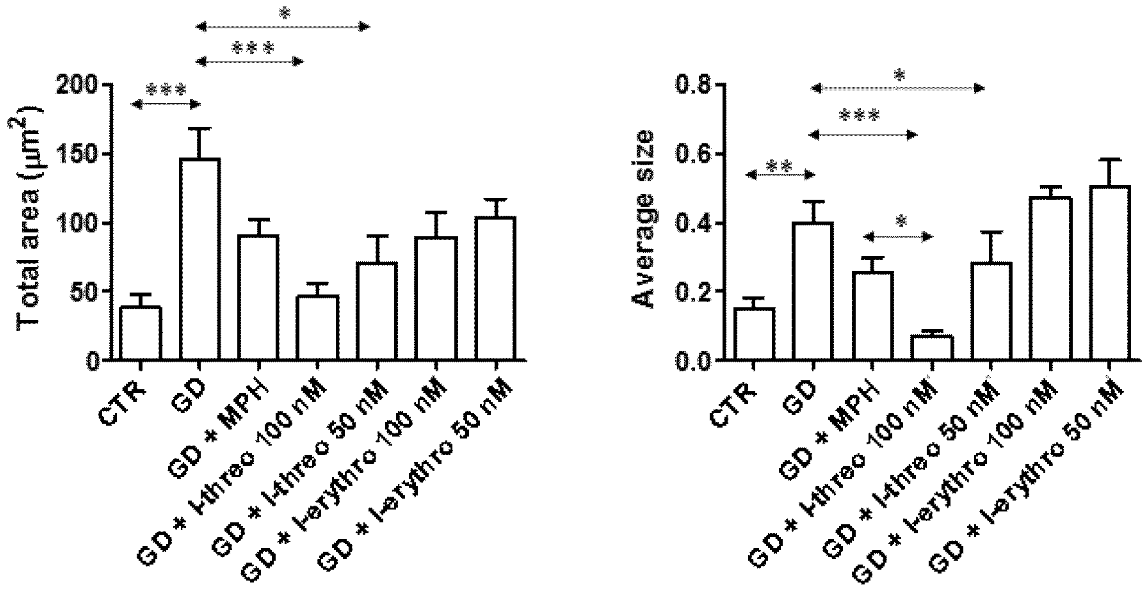
FIG. 4 shows that I-threo treatment efficiently hinders alpha-synuclein aggregation in primary mesencephalic neurons exposed to glucose deprivation in a concentration-dependent manner (* P<0.05,  P<0.01, * P<0.001, One-way ANOVA+Newman-Keuls' post comparison test).

It was found (FIG. 4) that 50 nM and even more 100 nM I-threo treatment was able to significantly reduce alpha-synuclein inclusion formation as detected by both total alpha-synuclein immunofluorescence intensity and alpha-synuclein-positive particle size. MPH and VI-threo did not reduce alpha-synuclein aggregation at any of the concentrations used. These results support that I-threo efficiency is 50-70% higher than that of MPH.

This evidence supports a concentration-dependent inhibitory activity of I-threo on alpha-synuclein aggregation in mouse primary mesencephalic neurons.

Evaluation of the Toxic Potential of the Different Mph Analogues

The cytotoxic effect of compounds treatment was measured by evaluating mitochondrial dehydrogenase activity using the MTT salt assay.

Neuronal differentiated SK—N—SH cells were thus exposed to different concentrations of I-threo, IV-threo, I-erythro, V-threo and V-erythro as described above, and then used for the MTT cell viability assay.

Animals: C57BL/6J wt mice (C57BL/6J) (Charles River, Wilmington, MA) used in this study, were bred in our animal house facility at the Department of Molecular and Translational Medicine of University of Brescia. Animals were maintained under a 12h light-dark cycle at a room temperature (rt) of 22° C. and had ad libitum food and water. All experiments were made in accordance to Directive 2010/63/EU of the European Parliament and of the Council of 22 Sep. 2010 on the protection of animals used. All experimental and surgical procedures conformed to the National Research Guide for the Care and Use of Laboratory Animals were approved by the Animal Research Committees of the University of Brescia (Protocol Permit 719/2015-PR). All achievements were made to minimize animal suffering and to reduce the number of animals used. Primary neuronal cultures from mesencephalic tissues were dissected from C57BL/6J 13-days embryos. Briefly, after mechanical dissociation the single cells were re-suspended in Neurobasal medium containing 100 μg/ml penicillin, 100 μg/ml streptomycin, 0.5 mM glutamine and 1% B27 supplement. Cells were then centrifuged and cell count and viability assays were performed using the Trypan Blue exclusion test. Cells were seeded onto poly-D-lysine-coated glass coverslides in 24-well plates (14 μg/mL) for immunocytochemistry (100000 cells/well). Cells were maintained at 37° C. under a humidified atmosphere of 5% CO2 and 95% 02 for at least 10 days in vitro (DIV 10) prior to their use to allow their maturation. At DIV 10, cells were treated with increasing concentrations (0.01 μM-0.1 μM-1 μM-10 M-100 M) of the different compounds (I-threo, IV-threo, I-erythro, V-threo, VI-threo). Twenty-four h after the treatments, culture medium was removed and 300 μL of MTT 0.5 mg/mL diluted in culture medium was added to each well. After 90' incubation at 37° C., the medium was removed and 250 μL aliquots of DMSO were added to each well to solubilize the formazan crystals. Absorbance was measured at 570 nm using a microplate reader. Cell viability was expressed as absorbance value.

Figure 5:
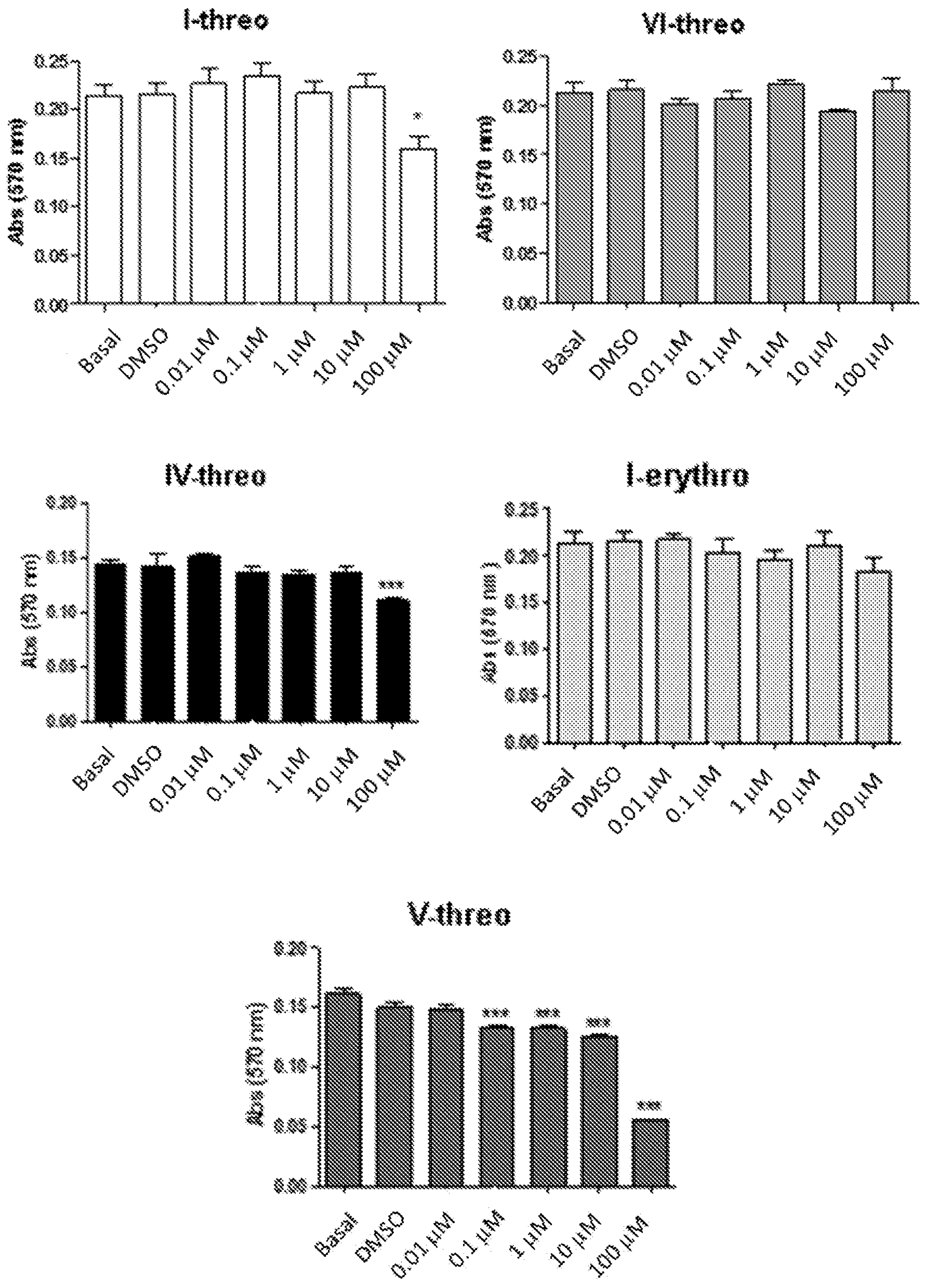
FIG. 5 shows MTT assays performed on primary mesencephalic cultures showed significant decrease in cell viability only at high or very high concentrations (100 μM) in the case of I-threo and IV-threo treatment. Only V-threo exhibited cytotoxicity at low concentrations. (* P<0.05 vs. Basal; *** P<0.001 vs. Basal; One-way ANOVA+Dunnett's post comparison test).

Results showed (FIG. 5) that I-threo and VI-threo did not exhibit toxic effects at the working concentrations reducing alpha-synuclein aggregation or stimulating alpha-synuclein/Synapsin III interaction. Only I-threo was found to reduce the cell viability of SK—N—SH cells at 100 μM concentration, that largely exceed those used for FRET or alpha-synuclein aggregation studies.

Among the other MPH derivatives, IV-threo exhibited the same profile of I-threo upon MTT test while I-erythro did not result toxic even when used at 100 μM concentration. V-threo instead, resulted markedly toxic starting from 0.1 μM concentration.

Evaluation of the Therapeutic Efficacy and Ec50 in Reducing Alpha-Synuclein Aggregation in Sk—N-Sh Cells of Compound I-Threo in Comparison with Mph It was then investigated the % effect in reducing alpha-synuclein aggregation of compound I-threo and MPH in order to have more indications on their efficacy and potency. Remarkably, results from these studies showed that, although the efficacy of the two compounds resulted almost comparable, compound I-threo EC50 is 200 fold lower than that of MPH ($4,312\times10^{-7}$ M vs $3,733\times10^{-5}$ M, Table 2), thus supporting a significantly higher potency for compound I-threo vs MPH (P<0.0001, F (1-138)=56.18, non-linear fit) (FIG. 6).

Evaluation of the Capacity of the Methylphenidate Derivatives VII-Threo, VII-Erythro, IX-Threo and X To Stimulate the Functional Interaction Between Alpha-Synuclein and Synapsin III in Neuronal-Like Cells Exhibiting Alpha-Synuclein/Synapsin III Co-Aggregates Human neuroblastoma SK—N—SH cells were grown in complete medium comprising Dulbecco's modified Eagle's medium with 1000 mg glucose/l supplemented with 10% heat-inactivated fetal bovine serum, 100 μg/ml penicillin and 100 μg/ml streptomycin. Cells were maintained at 37° C. under a humidified atmosphere of 5% CO2 and 95% 02. For FRET studies, SK—N—SH cells were seeded onto poli-D-lysine-coated 13 mm glass coverslips in 24-well plates (15000 cells per coverslip) and were maintained in differentiation medium for ten days by daily adding 10 μM retinoic acid to the medium. At day 7, cells were transiently transfected with pGFP-human Synapsin III (transducing human green fluorescent protein (GFP)-tagged Synapsin III and pCMV6-RFP-alpha-synuclein (transducing red fluorescent protein (RFP)-tagged alpha-synuclein) constructs, by using Lipofectamine 3000, according to the manufacturer's instructions. pCMV6-RFP-alpha-synuclein single-transfected cells were used as negative controls during the FRET experiments. Three days after transfection, cells were treated for 15 min with vehicle (normal saline 0.9%-control), 10 μM MPH (d-threo), 10 μM I-threo, 10 μM IV-threo, 10 μM I-erythro, 10 μM V-threo or 10 μM VI-threo, then immediately fixed with Immunofix for 15 min and subsequently mounted on glass slides. Fixed cells were analyzed by means of a Zeiss confocal laser microscope LSM 880 (Carl Zeiss) with the laser set on λ=488-543. After identifying double positive cells three-to-six regions of interest (ROI) were analyzed for 4 series. Two images of basal condition (Pre-bleaching) were acquired before bleaching the RFP acceptor fluorophore with laser 543 set at 65% power. Then, other two images were acquired after the bleaching (Post-bleaching). The FRET efficiency (intended as the GFP recovery after RFP photobleaching) was measured by using Zen black software (Carl Zeiss). The average intensity of the background (outside the cell) was subtracted from the average intensity of the ROI and all the FRET values resulting from the different ROI were used for statistical analysis.

Analysis of the acceptor photobleaching FRET experiments showed (FIG. 7) that similarly to what has been shown for compound I-threo, the compound VII-threo and IX-threo were able to significantly increase the interaction between alpha-synuclein and Synapsin III measured at % FRET efficiency changes when compared to MPH-treated neuronally differentiated SK—N—SH cells (+4.3%, P<0.05 and +4.6%, P<0.05, respectively. One-way ANOVA+Newman-Keuls multiple comparison test).

Figure 8:
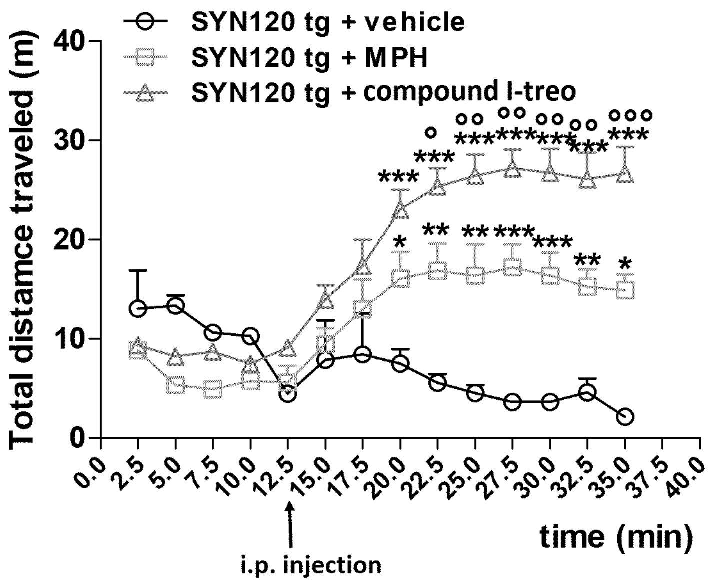
FIG. 8 shows the histogram that summarize the effect of acute i.p. injection of vehicle, MPH or I-threo (10 mg/kg) on the locomotor activity of SYN120 tg mice in an open field arena (*, *** P<0.05, <0.01, <0.001 vs vehicle. °, °°,°°° P<, 0.05, 0.01, 0.001 vs MPH;, One-way ANOVA+Bonferroni post comparison test)

In Vivo Evaluation of the Capacity of Compound I-Threo to Promote the Motility of a Parkinson'S Disease Mouse Model We investigated the ability of compound I-threo to stimulate the motility of Parkinson's disease mice more efficiently that MPH. To this purpose we used mice transgenic for human C-terminally truncated alpha-synuclein (SYN120 tg mice) a model where we previously showed the presence of alpha-synuclein/Synapsin III co-aggregation. All experiments were made in accordance with Directive 2010/63/EU of the European Parliament and of the Council of 22 Sep. 2010 on the protection of animals used. All experimental procedures conformed to the National Research Guide for the Care and Use of Laboratory Animals and were approved by the Animal Research Committees of the University of Brescia (Protocol Permit 719/2015-PR). Three different groups of 12 month-old SYN120 tg mice (N=3 animals per group) were used for the motility assay by using the open-field behavioural paradigm. The motility of the animals in the open-field arena was registered and analysed by using the Any-Maze system. After recording the basal activity of the mice for 12.5 minutes, the animals were intraperitoneally (i.p.) injected with vehicle or MPH (10 mg/kg) or compound I-threo (10 mg/kg) and their activity was registered for the following 22.5 minutes. The total distance travelled by the mice during 2.5 minutes intervals was plotted on graphs. The results of these studies (FIG. 8) showed that compound I-threo was able to improve the motility of SYN120 tg mice more efficiently than MPH (*, , * P<0.05, <0.01, <0.001 vs vehicle. °, 00,00° P<, 0.05, 0.01, 0.001 vs MPH).

Figure 9:
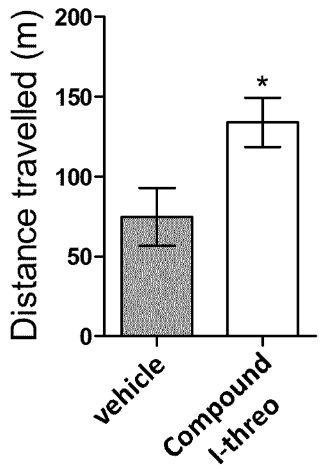
FIG. 9 shows that graph with the total distance travelled by SYN120 tg mice in an open field area after 6 weeks chronic treatment with I-threo (daily i.p. 5 mg/kg; * P<0.05. Student's t-test).

Evaluation of the Effect of a Chronic 6 Weeks Treatment with Compound I-Threo on Motility, Nigrostriatal Alpha-Synuclein Pathological Deposition and Striatal Dopaminergic Fibers in The Syn120 Tg Mouse Model of Parkinson'S Disease Two groups of 12 month-old SYN120 tg mice (N=4 animals per group) were subjected to daily i.p. administration of either vehicle or compound I-threo (5 mg/kg) for 6 weeks. All experiments were made in accordance with Directive 2010/63/EU of the European Parliament and of the Council of 22 Sep. 2010 on the protection of animals used. All experimental or surgical procedures conformed to the National Research Guide for the Care and Use of Laboratory Animals and were approved by the Animal Research Committees of the University of Brescia (Protocol Permit 719/2015-PR). At the end of treatment, the total distance travelled by the mice was recorded in the open field arena. Of note we found that the SYN120 tg mice treated with compound I-threo exhibited a significant improvement in total motility evaluated as total distance travelled (FIG. 9). * $P<0.05$. Student's t-test. N=3 for each experimental group.

After the behavioral studies animals were sacrificed by transcardiac perfusion to collect their brains, which were used for immunohistochemical studies aimed at evaluating the efficacy of compound I-threo to reduce pathological alpha-synuclein deposition and neuroprotection in the nigrostriatal system.

Figure 10:
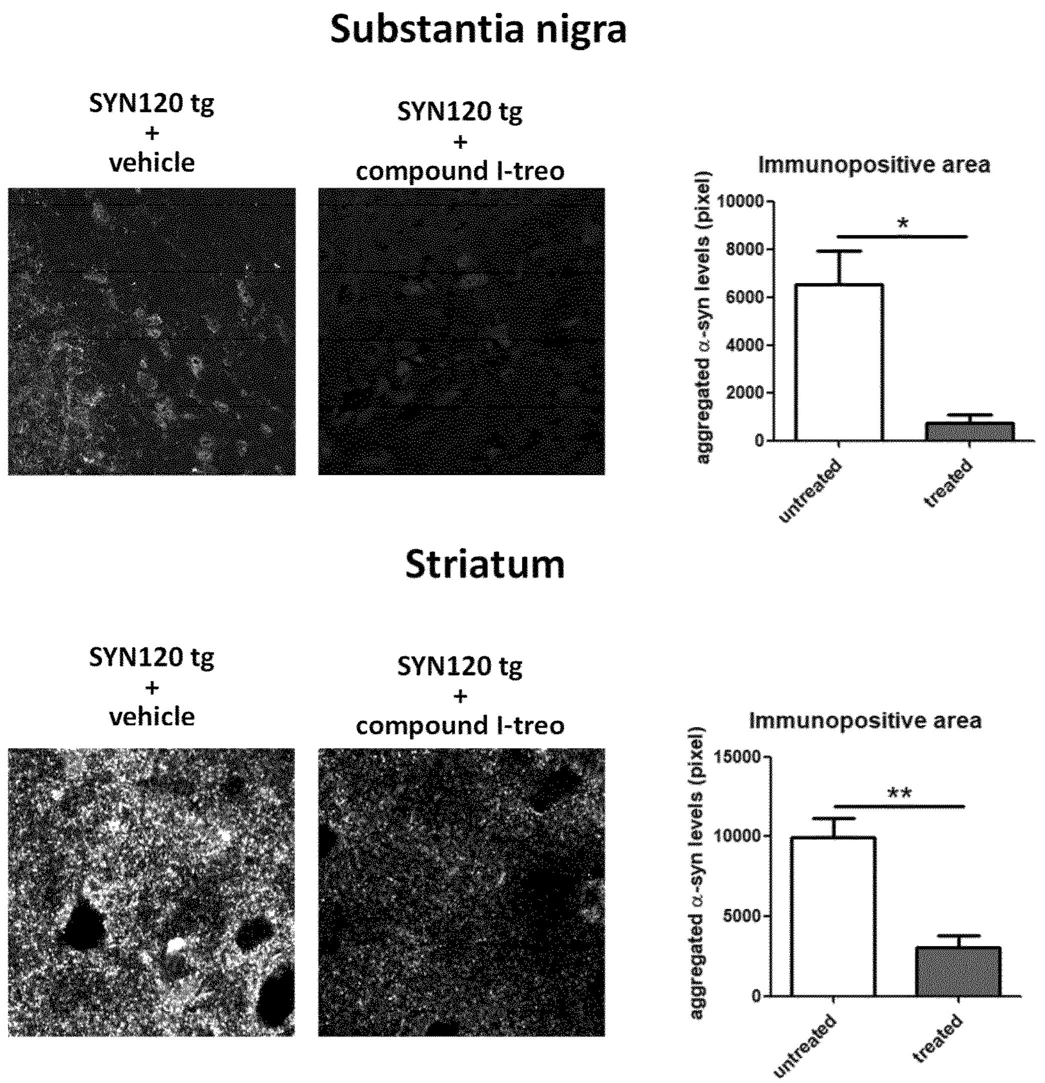
FIG. 10 shows representative images and quantifications (graphs) of aggregated alpha-synuclein in the substantia nigra and striatum of SYN120 tg mice chronically treated with vehicle or I-threo (daily for 6 weeks i.p. 5 mg/kg; (* P<0.05, ** P<0.01, Student's t-test).

First, we quantified aggregated alpha-synuclein pathological deposition by using an antibody specifically recognizing aggregated alpha-synuclein in the subtantia nigra and striatum of mice. Results from these investigations (FIG. 10) showed that after the chronic treatment with compound I-threo there was a statistically significant reduction of aggregated alpha-synuclein in both the substantia nigra and striatum (* $P<0.05$, ** $P<0.001$, Student's t-test).

Figure 11:
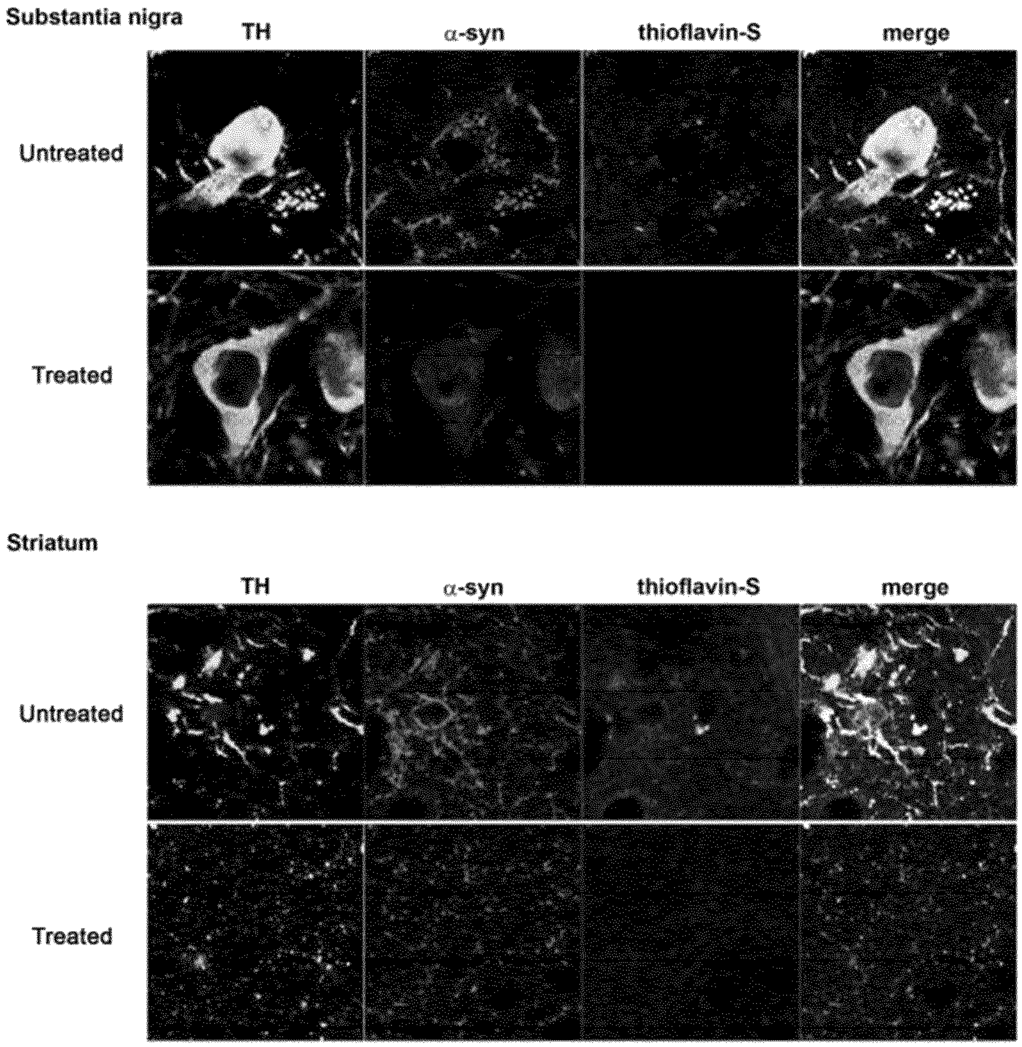
FIG. 11 shows representative images of Thioflavin-S signal in the substantia nigra and striatum of SYN120 tg mice chronically treated with vehicle or I-threo (daily for 6 weeks i.p. 5 mg/kg).

Then alpha-synuclein aggregation was evaluated also by using Thioflavin-S a dye recognizing fibrillary aggregates. Of note we found a marked reduction of thioflavin-S signal (in green) in correspondence to the total alpha-synuclein immunopositive areas (in red) in the substantia nigra and striatum of the mice that were treated with compound I-threo (FIG. 11). Please note that dopaminergic neurons or fibers in the images were labelled in light blue.

Finally, we evaluated the neuroprotective effect of the chronic treatment with compound I-threo by quantifying the recovery of striatal dopaminergic fibers in the SYN120 tg mice treated with the compound when compared to the vehicle-treated animals.

Figure 12:
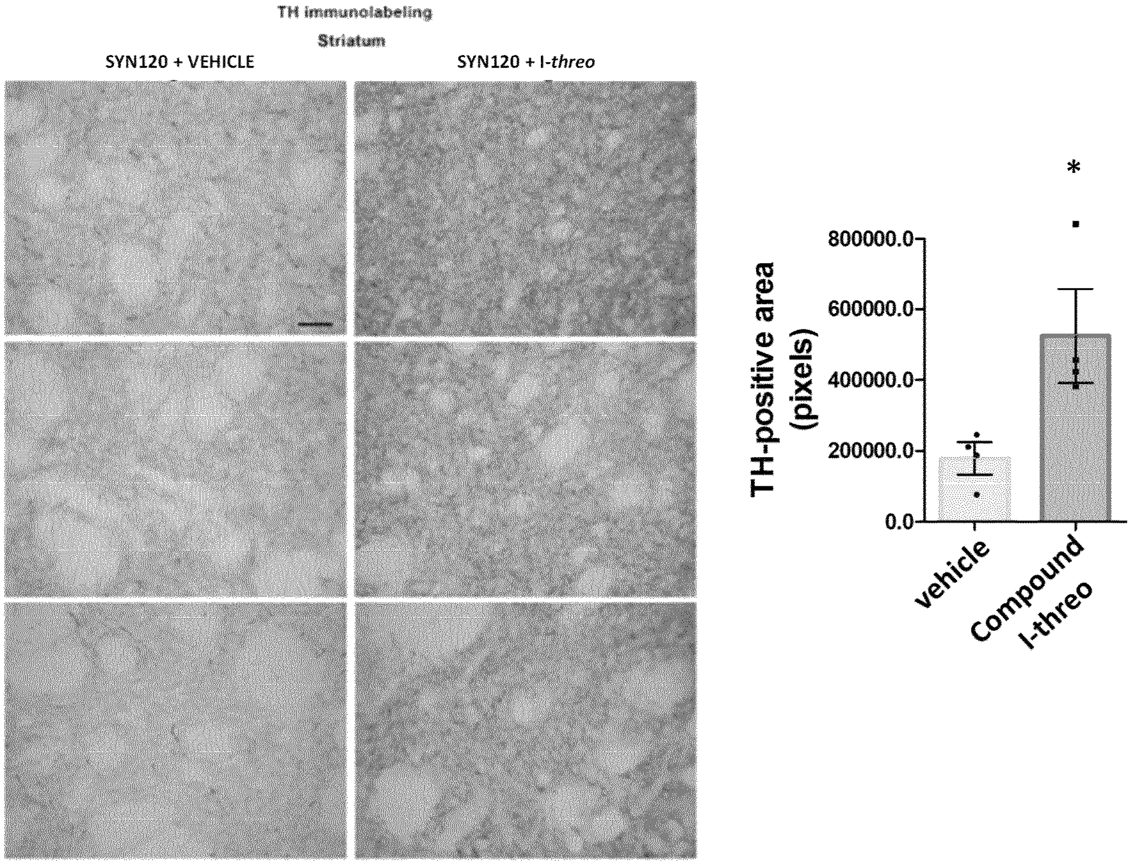
FIG. 12 shows representative pictures and quantifications (graphs) of TH-positive fibers in the striatum of SYN120 tg mice chronically treated with vehicle or I-threo (daily for 6 weeks i.p. 5 mg/kg; * P<0.05, Student's t-test).

We observed that the SYN120 tg mice chronically treated with compound I-threo exhibited a significant recovery of striatal TH-positive dopaminergic fibers when compared to the vehicle-treated littermates (FIG. 12,* $P<0.05$, Student's t-test). These results in their complex support that the novel MPH derivatives, by reducing alpha-synuclein aggregation and protecting nigrostriatal neurons, can exert a disease modifying effect in Parkinson's disease. In addition, they are able to stimulate the motor activity of Parkinson's disease mice, thus supporting that they can significantly improve Parkinson's disease motor symptoms.

The invention claimed is:

1. A disease-modifying method of treating Parkinson's disease to reduce alpha-synuclein aggregation and stimulate the functional interaction between alpha-synuclein and Synapsin III, the method comprising administering to a subject in need thereof an effective amount of a disease-modifying agent compound of formula (A), said formula (A)

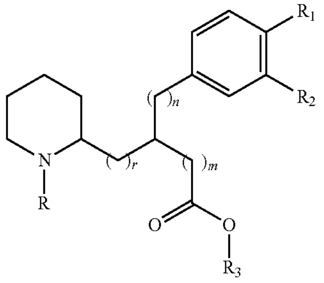

(A)

wherein
R is selected from the group consisting of H, and Alk;
$R_1$ is selected from the group consisting of H, Alk, OAlk, and Ar;
$R_2$ is selected from the group consisting of H, Alk, OAlk, and Ar;
$R_1$ and $R_2$ joined together can form an (hetero) aromatic ring;
$R_3$ is selected from the group consisting of Me, Et, Pr and i-Pr;
n is 0 or 1; m is 0 or 1; r is 0 or 1;
Alk is a linear or branched $C_1$-$C_4$ alkyl;
Ar is a 5 or 6 membered (hetero) aromatic ring;
including pharmaceutical acceptable salt thereof,
including threo and erythro racemates and (R,R) or (S,S) stereoisomers thereof,
excluding methyl 2-phenyl-2-piperidin-2-ylacetate.

2. The method according to claim 1 wherein
Alk is Me or Et;
Ar is Ph, thiophene or furane.

3. The method according to claim 1 wherein
R is selected from the group consisting of H and Me;
$R_1$ is selected from the group consisting of H, Me, OMe, and Ph;
$R_2$ is selected from the group consisting H, H and Me;
$R_1$ and $R_2$ joined together can form a phenyl ring.

4. The method according to claim 1 wherein
$R_1$ is other than H; and
$R_2$ is H.

5. The method according to claim 1 wherein
R is H;
$R_1$ is Me;
$R_2$ is H;
$R_3$ is Me;
n is 0, m is 0 and r is 0.

6. The method according to claim 1 wherein
R is Me;
$R_1$ is Me;
$R_2$ is H;
$R_3$ is Me;
n is 0, m is 0 and r is 0.

7. The method according to claim 1 wherein
R is H;
$R_1$ is H;
$R_2$ is H;
$R_3$ is Me;
n is 1, mis 0 and r is 0.

8. The method according to claim 1 wherein the compound of formula (A) has a threo configuration.

9. The method according to claim 1 selected in the group consisting of

I-threo

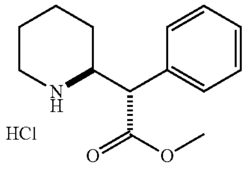

,

VI-threo

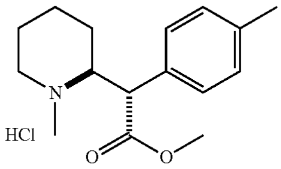

, and

-continued

VII-threo

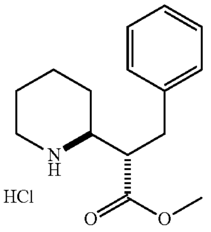

.

10. The method as in claim 1, comprising administering to a subject in need thereof a pharmaceutical composition comprising an effective amount of a disease-modifying agent compound of formula (A) as defined in claim 1.

11. The method according to claim 8 wherein the compound of formula (A) has a threo configuration and is the (R,R) stereoisomer.

* * * * *